(12) United States Patent
Ko et al.

(10) Patent No.: US 11,992,511 B2
(45) Date of Patent: May 28, 2024

(54) LACTOBACILLUS PARACASEI STRAIN AND USE THEREOF

(71) Applicant: KoBioLabs, Inc., Seoul (KR)

(72) Inventors: Gwang Pyo Ko, Seoul (KR); Woonki Kim, Ulsan (KR); You-Jin Jang, Seoul (KR); Boram Seo, Gyeonggi-do (KR); June-Chul Lee, Gyeonggi-do (KR); Tae-Wook Nam, Gyeonggi-do (KR); Insu Kim, Gyeonggi-do (KR); Jin-Woo Lee, Gyeonggi-do (KR)

(73) Assignee: KoBioLabs, Inc., Seoul (KR)

( * ) Notice: Subject to any disclaimer, the term of this patent is extended or adjusted under 35 U.S.C. 154(b) by 0 days.

(21) Appl. No.: 17/673,460

(22) Filed: Feb. 16, 2022

(65) Prior Publication Data

US 2022/0175857 A1    Jun. 9, 2022

Related U.S. Application Data

(63) Continuation of application No. 17/093,556, filed on Nov. 9, 2020, now Pat. No. 11,291,698, which is a continuation of application No. PCT/KR2019/005553, filed on May 9, 2019.

(30) Foreign Application Priority Data

May 9, 2018   (KR) .................. 10-2018-0053279

(51) Int. Cl.
| | |
|---|---|
| A61K 35/747 | (2015.01) |
| A23L 33/00 | (2016.01) |
| A23L 33/135 | (2016.01) |
| A61P 1/00 | (2006.01) |
| A61P 37/08 | (2006.01) |
| C12N 1/20 | (2006.01) |
| A61K 35/00 | (2006.01) |
| C12R 1/225 | (2006.01) |

(52) U.S. Cl.
CPC .......... *A61K 35/747* (2013.01); *A23L 33/135* (2016.08); *A23L 33/40* (2016.08); *A61P 1/00* (2018.01); *A61P 37/08* (2018.01); *C12N 1/20* (2013.01); *C12N 1/205* (2021.05); *A23V 2002/00* (2013.01); *A23V 2400/165* (2023.08); *A61K 2035/115* (2013.01); *C12R 2001/225* (2021.05)

(58) Field of Classification Search
None
See application file for complete search history.

(56) References Cited

U.S. PATENT DOCUMENTS

| | | | |
|---|---|---|---|
| 5,952,021 A | 9/1999 | Santus | |
| 7,026,161 B2 | 4/2006 | Park | |
| 7,090,840 B2 | 8/2006 | Cho | |
| 7,195,906 B2 | 3/2007 | Collins et al. | |
| 8,361,481 B2* | 1/2013 | Hara .................. | A23L 33/135 |
| | | | 424/234.1 |
| 11,291,698 B2 | 4/2022 | Ko et al. | |
| 2010/0034877 A1 | 2/2010 | Alenfall et al. | |
| 2015/0238548 A1 | 8/2015 | Huang et al. | |

FOREIGN PATENT DOCUMENTS

| | | |
|---|---|---|
| CN | 102143756 A | 8/2011 |
| CN | 102168048 A | 8/2011 |
| CN | 106103696 A | 3/2015 |
| CN | 104894021 A | 9/2015 |
| CN | 107308190 A | 11/2017 |
| CN | 113260372 A | 8/2021 |
| CN | 114867842 A | 8/2022 |
| EP | 0415941 B1 | 6/1963 |
| EP | 0554418 | 3/1998 |
| EP | 1468075 B1 | 12/2005 |
| EP | 2581461 | 4/2013 |
| EP | 3912631 A1 | 11/2021 |
| JP | 2009511471 | 3/2009 |
| JP | 2014516589 | 7/2014 |
| KR | 10-0419132 B1 | 2/2004 |
| KR | 10-0786364 B1 | 12/2007 |
| KR | 20160008060 A | 1/2016 |

(Continued)

OTHER PUBLICATIONS

Yang, J., et al., "Regulating Effect of Lactobacillus paracasei L9 on Th1/Th2 Balancing in Allergic Mouse's Splenocytes", Journal of Chinese Institute of Food Science and Technology, 17(4): 14-20, Apr. 2017.

Akaguma, M., et al., "Complementary effect of oral administration of Lactobacillus paracasei K71 on canine atopic dermatitis", Jpn J Vet Dermatol, 2013, 19(3): 155-158.

Luster M.I. et al. "Immunotoxicology", Encyclopedia of Immunology (Second Edition), 1998, pp. 1365-1369.

Corrected Notice of Allowability for U.S. Appl. No. 17/093,556, entitled "Lactobacillus Paracasei Strain and Use Thereof;" mailed on Feb. 25, 2022.

(Continued)

*Primary Examiner* — Vera Afremova
(74) *Attorney, Agent, or Firm* — Hamilton, Brook, Smith & Reynolds, P.C.

(57) ABSTRACT

Human-derived probiotic strains *Lactobacillus paracasei* KBL382, *Lactobacillus paracasei* KBL384 and *Lactobacillus paracasei* KBL385 are described, as well as uses of the strains for improving intestinal health and treating or preventing intestinal diseases. The strains have excellent anti-inflammatory and immunomodulatory functions, superb strengthening effects on tight junctions of the intestinal tract wall, suppress enteritis-induced weight loss and colon length reduction, thereby exhibiting therapeutic effects for enteritis, and significantly alleviate the symptoms of atopic dermatitis. The strains can be used as probiotic material for enhancing anti-inflammatory effects, strengthening immunity, improving intestinal health functions, and alleviating allergic diseases.

17 Claims, 18 Drawing Sheets

Specification includes a Sequence Listing.

(56) References Cited

FOREIGN PATENT DOCUMENTS

| KR | 10-1614262 | B1 | 4/2016 |
|----|-----------|----|--------|
| KR | 10-1810138 | B1 | 12/2017 |
| RU | 2607370 | C1 | 3/2014 |
| WO | 96/29083 | | 9/1996 |
| WO | 2015159240 | A1 | 10/2015 |
| WO | 2017125447 | | 7/2017 |

OTHER PUBLICATIONS

Corrected Notice of Allowability for U.S. Appl. No. 17/093,556, entitled "Lactobacillus Paracasei Strain and Use Thereof;" mailed on Feb. 24, 2022.

D'Arienzo, R., et al., "Distinct immunomodulatory properties of Lactobacillus paracasei strains", Journal of Applied Microbiology, vol. 111, pp. 1482-1491, 2011.

Kim, W.-K. et al. Administration of Lactobacillus paracasei strains improves imrmmomodulation and changes the composition of gut microbiola leading to improvement of colitis in mice. Journal of Functional Foods. 2019, vol. 52, pp. 565-575.

Kim K et al., "Inhibitory mechanism of anti-allergic peptides in RBL2H3 cells", Eur J Pharmacol, 581:191-203, 2008.

NCBI. GenBank accession No. MG551239.1, "Lactobacillus paracasei strain NWAFU1561 16S ribosomal RNA gene, partial sequence", (Nov. 26, 2017).

NCBI. GenBank accession No. KF544958.1, "*Lactobacillus paracasei* subsp. tolerans strain FX-6 16S ribosomal RNA gene, partial sequence", (Aug. 9, 2014).

NCBI. GenBank accession No. KU315074.1, "Lactobacillus paracasei strain PN3 16S ribosomal RNA gene, partial sequence", (Apr. 26, 2016).

Report of a joint FAO/WHO working group on drafting guidelines for the evaluation of probiotics in food, London Ontario, Canada, 2002.

International Search Report for International Application No. PCT/KR2019/005553, "Lactobacillus Paracasei Strain and Use Thereof", dated Aug. 19, 2019.

International Preliminary Report on Patentability for International Application No. PCT/KR2019/005553, "Lactobacillus Paracasei Strain and Use Thereof", dated Nov. 10, 2020.

U.S. Notice of Allowance for U.S. Appl. No. 17/093,556, entitled "Lactobacillus Paracasei Strain and Use Thereof;" mailed on Nov. 24, 2021.

Search Report for Malaysia Application No. PI2020005819, "Lactobacillus Paracasei Strain and Use Thereof" Dated Feb. 25, 2021. 1 page.

U.S. Non-Final Office Action for U.S. Appl. No. 17/093,556, entitled "Lactobacillus Paracasei Strain and Use Thereof;" mailed on Mar. 23, 2021.

U.S. Final Office Action for U.S. Appl. No. 17/093,556, entitled "Lactobacillus Paracasei Strain and Use Thereof;" mailed on Jul. 12, 2021.

Ekmekciu, I. et al., "Amelioration of Intestinal and Systemic Sequelae of Murine Campylobacter Jejuni Infection by Probiotic VSL#3 Treatment," Gut Pathog. 9:17; pp. 1-13 (2017).

Supplementary European Search Report for EP Application No. 19798873, "Lactobacillus Paracasei Strain and Use Thereof", dated Dec. 3, 2021.

\* cited by examiner

LACTOBACILLUS PARACASEI STRAIN AND USE THEREOF

RELATED APPLICATIONS

This application is a continuation of U.S. application Ser. No. 17/093,556, filed on Nov. 9, 2020, which is a continuation of International Application No. PCT/KR2019/005553, which designates the United States and was filed on May 9, 2019, published in Korean and claims priority under 35 U.S.C. § 119 or 365 to Korean Application No. 10-2018-0053279, filed May 9, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
   a) File name: 58881000002_SEQUENCE_LISTING.TXT; created Jan. 6, 2022, 9,063 Bytes in size.

TECHNICAL FIELD

The present invention relates to strains of *Lactobacillus paracasei* and the use thereof. More specifically, the present invention relates to a health functional food composition for alleviation of allergic symptoms, improvement of immunoregulation, alleviation of inflammatory symptoms, alleviation of atopic dermatitis, and improvement of intestinal health; and a pharmaceutical composition for the treatment or prevention of allergic diseases, autoimmune diseases, inflammatory diseases, atopic dermatitis and/or intestinal diseases, comprising an effective amount of at least one selected from the group consisting of a *Lactobacillus paracasei* KBL382 strain, a *Lactobacillus paracasei* KBL384 strain, a *Lactobacillus paracasei* KBL385 strain, microbial cells of said strain, cultures of said strain, lysates of said strain, and extracts of said strain.

BACKGROUND

Probiotics refer to microorganisms and the resulting products therefrom having anti-bacterial activities and enzyme activities to help the balance of intestinal microorganisms. In addition, probiotics are also defined as live bacteria in the form of a single or multiple strain(s) to improve intestinal flora when provided to human or animals in the form of dry cells or fermentation products. Probiotics must inhabit the human gut, be non-pathogenic and non-toxic, and survive long enough until they arrive at the intestine. Further, probiotics must maintain viability and activities until they are consumed in the food delivered, be sensitive to antibiotics used to prevent infection, and not have antibiotic-resistant plasmids. Also, probiotics must be resistant to acids, enzymes, and bile in the intestinal environment.

These probiotics may include, for example, *Bacillus* sp. having an excellent ability to produce digestive enzymes such as amylase, protease, lipase, cellulase, and phosphatase, *Lactobacillus* sp. producing lactic acid, and photosynthetic bacteria preventing stink by way of using the stink-causing substances (such as ammonia, hydrogen sulfide, and amines) remaining in the feces of livestock in metabolic process.

In particular, *Bacillus* sp. and *Lactobacillus* sp. are known as very useful probiotics because they include strains that produce various antibacterial substances. These lactic acid bacteria produce antimicrobial peptides called Bacteriocin, which have antibacterial mechanisms that are not related to the mechanism of antibiotic resistance. Bacteriocins have polymorphic characteristics that their molecular weights, biochemical properties, and antimicrobial ranges and mechanisms for the host vary considerably. Klaenhammer defines bacteriocin as a protein or protein complex that has direct antibacterial activity against species close to bacteriocin-producing bacteria.

Meanwhile, irritable bowel syndrome (IBS) is a symptom characterized by abdominal pain, and/or irritations associated with changed intestinal movement or bowel habits, such symptoms cannot be explained with anatomic or biochemical abnormality. Common symptoms of IBS also include urinary urgency, bloating and feeling of incomplete intestinal movement. Accordingly, IBS can be classified as functional gastrointestinal disorders comprising conditions such as functional bloating, non-cardiac chest pain, non-ulcerative dyspepsia, and chronic constipation or diarrhea. In particular, in the case of IBS, since the related symptoms affect both well-being and normal functional aspect of patients, the disease has a huge impact on morbidity and quality of life, beyond abdominal pain and discomfort.

Inflammatory bowel disease (IBD) is a condition in which abnormal chronic inflammation in the intestine repeats improvement and recurrence, comprising all intestinal inflammatory diseases, such as Crohn's disease, ulcerative colitis, or Behcet's disease, but not limited thereto. Many researches have been conducted in the field of drug development to treat IBS and IBD. In this regard, various antidepressants are commonly used, even though the efficacy thereof in clinical trials is moderate and the clinical utility thereof is limited due to significant side effects. Serotonergic medications have also been proved to have efficacy against overall IBS symptoms. However, the application of these medications has been restricted in various ways due to recent several safety problems. Accordingly, there is increasing interest in developing a new therapeutic agent for IBS.

Meanwhile, allergy is a biochemical phenomenon that exhibits a unique, altered response to a foreign substance (antigen, allergen). The foreign substance which causes symptoms is called allergen, while the diseases from those symptoms are called allergic diseases. Allergy is a pathological process in the living body resulting from the antigen-antibody reaction. In general, there are four types of allergies depending on the period to trigger the reaction and the complement involvement. Type 1, among those, is anaphylactic type (immediate type) in which target organs are mostly digestive organs, skin and lungs, and the common symptoms include gastrointestinal allergy, urticaria, atrophodermatitis, allergic rhinitis, and bronchial asthma, etc. The pathological mechanism of Type 1 is known as follows: when antigens contact IgE antibodies attached to the surface of mast cells and basophilic leukocytes, the target cells are activated to secrete chemical transmitters such as histamine, leukotriene, and PAF, and then blood vessels and smooth muscles are contracted. Such mechanism can be often combined with Type 4 (delayed type). In other words, such anaphylaxis and allergic reaction can arise due to a variety of changes in the mast cells, etc. The activation of mast cells, which leads to degranulation, is caused by binding of antigen, anti-IgE, lectin, etc. to Fc receptors, stimulation of anaphylatoxin, etc., or other drugs such as calcium ionophore, compound 48/80, codeine and synthetic adrenocorticotropic hormone.

Mast cells and basophils in blood are known as main cells in the body to cause many allergic diseases such as allergic rhinitis, allergic dermatitis, asthma, food allergy and anaphylactic shock. These cells have receptors (FcRI) for IgE on their surfaces which is an antibody causing allergy, and the cells are stimulated by the allergy-causing substances (antigen, allergen) to secrete their own various allergy-causing substances out of the cells (Kim K et al, Eur J Pharmacol, 581:191-203, 2008).

Among allergic diseases, atopic dermatitis, as widely known to the public, is a chronic recurrent skin disease that affects newborns or children and may persist until adulthood. Like asthma or allergic rhinitis, atopic dermatitis is an inflammatory skin disease associated with local infiltration of T-lymphocyte which produces IL-4 and IL-5. IL-4 controls the development of the T helper 2 (Th2) phenotype, resulting in overproduction of immunoglobulins (Ig) and eosinophilia, and increase of serum IgE levels. 80-90% of the subjects who were positive to the skin test regarding food and inhalant allergens were found to have atopic dermatitis.

There are different treatments for treating or preventing allergic diseases including atopic dermatitis, but no effective treatment has been found yet. Some drug-based treatments are known, but even a short term administration of the drug for the treatment would develop a tolerance and a long-term administration may cause serious side effects, and thus such drug-based treatments of allergic diseases have been avoided recently. Under the circumstances, without treatment having any absolute, obvious effect, irritating symptoms such as itching and redness of skin in addition to allergy often fail to improve.

WO 96/29083 and EP 554418 disclose two types of *Lactobacillus* strains which form colonies in bowel, i.e., *Lactobacillus plantarum* 299v (DSM 6595) and *Lactobacillus casei* ssp. *rhamnosus* 271 (DSM 6594), etc. EP 415941 discloses a method for preparing a nutrient composition, comprising treating oat gruel with enzymes before mixing it with *lactobacilli*. U.S. Pat. No. 7,195,906 discloses a strain of *Bifidobacterium* isolated from resected and washed human gastrointestinal tract for the treatment of inflammatory diseases, especially gastrointestinal inflammation such as IBD and IBS.

However, no strain having excellent effects on improving intestinal health, for example, treatment of IBD and IBS, and on alleviating allergic symptoms has been found yet, and in order to find strains having such effects, many research institutions have been working on.

Under the circumstances, the present inventors screened a variety of strains based on the fact that a health improvement effect of probiotics is not general attributes of genus and species but rather is strain specific (Report of a joint FAO/WHO working group on drafting guidelines for the evaluation of probiotics in food, London Ontario, Canada, 2002), and identified a novel strain having excellent effects on immunoregulation, anti-inflammation activities, alleviation of allergy, improvement of intestinal health and treatment of intestinal diseases. Then, the present invention was completed by confirming superior effects of these strains.

SUMMARY

The purpose of the present invention is to provide a novel strain useful for improvement of intestinal health, treatment or prevention of intestinal diseases, improvement of immunoregulation, treatment or prevention of autoimmune diseases, alleviation of allergic symptoms, alleviation of inflammatory symptoms, alleviation and treatment of atopic dermatitis.

In order to achieve the purpose, the present invention provides a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP).

Also, the present invention provides a food composition or food additive composition comprising an effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides a pharmaceutical composition for the treatment or prevention of intestinal diseases, comprising an effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides a pharmaceutical composition for the treatment or prevention of allergic diseases, comprising an effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides a pharmaceutical composition for the treatment or prevention of autoimmune diseases or inflammatory diseases, comprising an effective amount of at least one selected from the group consisting of a *Lactobacillus paracasei* KBL382 strain (Accession No. KCTC13509BP), a *Lactobacillus paracasei* KBL384 strain (Accession No. KCTC13510BP), a *Lactobacillus paracasei* KBL385 strain (Accession No. KCTC13511BP), cultures of said strain, lysates of said strain, and extracts of said strain.

The present invention also provides a method for treating intestinal diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain to a subject in need thereof.

The present invention also provides a method for treating allergic diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain to a subject in need thereof.

The present invention also provides a method for treating autoimmune diseases or inflammatory diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), a *Lactobacillus paracasei* KBL385 strain (Accession No. KCTC13511BP), cultures of said strain, lysates of said strain, and extracts of said strain to a subject in need thereof.

The present invention also provides a composition for the use of preventing or treating intestinal diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides a composition for the use of preventing or treating allergic diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides a composition for the use of preventing or treating autoimmune diseases or inflammatory diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also provides the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), a *Lactobacillus paracasei* KBL385 strain (Accession No. KCTC13511BP), cultures of said strain, lysates of said strain, and extracts of said strain, for preparing a preventive or therapeutic drug for intestinal diseases.

The present invention also provides the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain, for preparing a preventive or therapeutic drug for allergic diseases.

The present invention also provides the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain, for preparing a preventive or therapeutic drug for autoimmune diseases or inflammatory diseases.

DETAILED DESCRIPTION

Figure 1B:
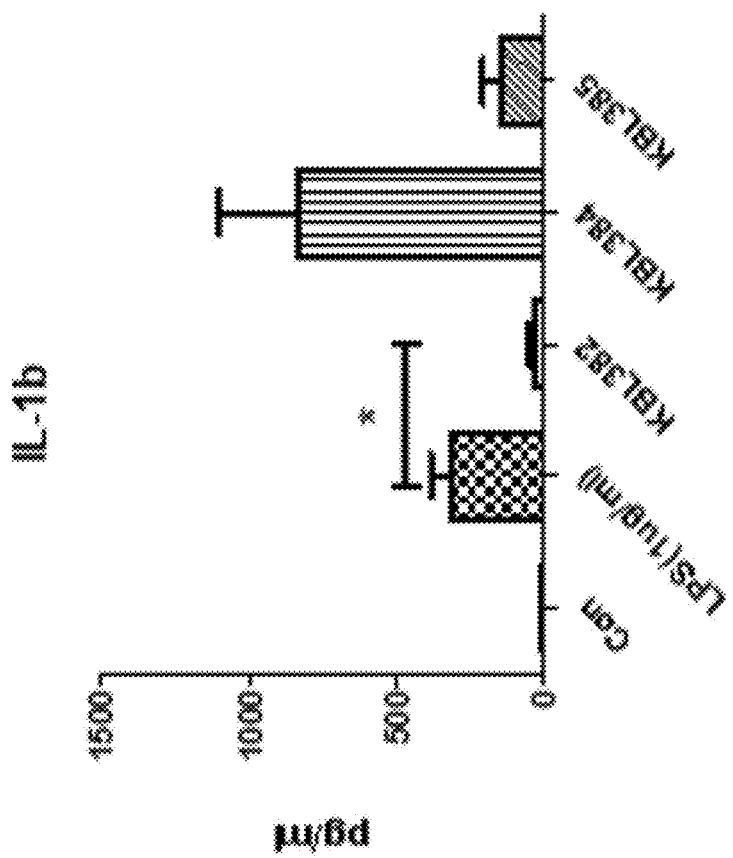
FIGS. 1A-1E illustrate the results confirming the effect of controlling inflammatory cytokines by a KBL382 strain, a KBL384 strain and a KBL385 strain of the present invention in PBMC.
Figure 1A:
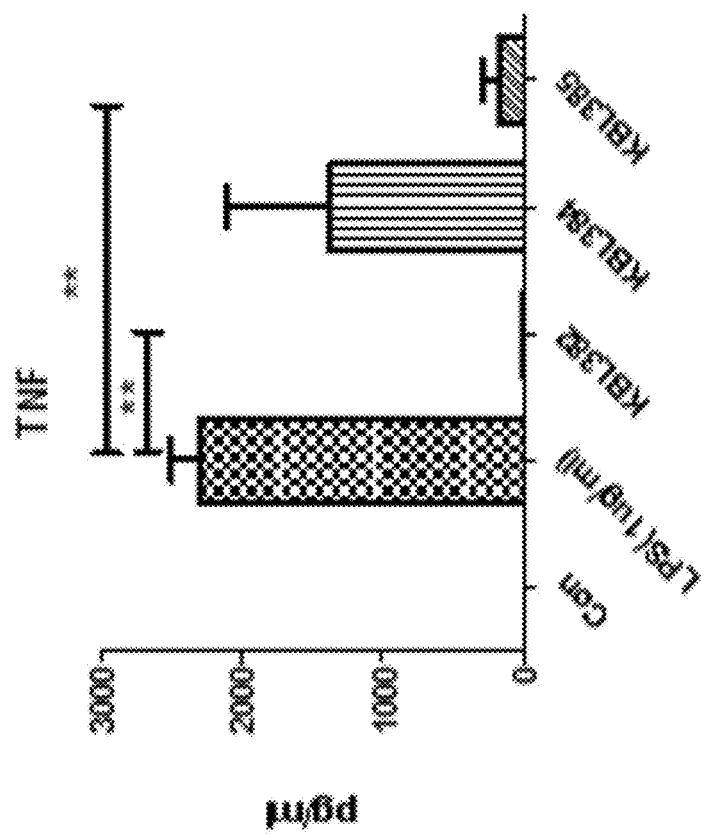
Figure 1D:
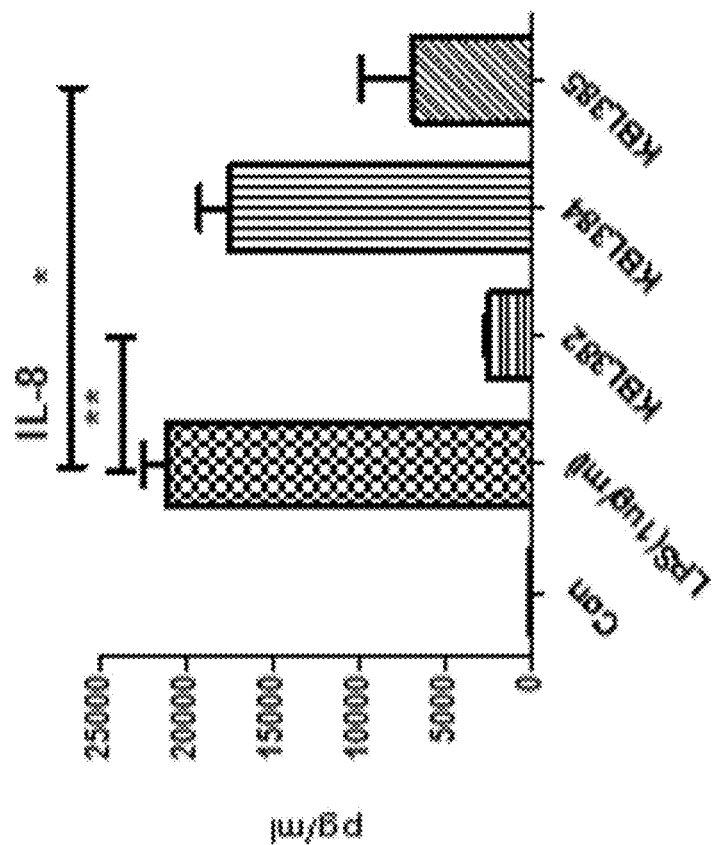
Figure 1C:
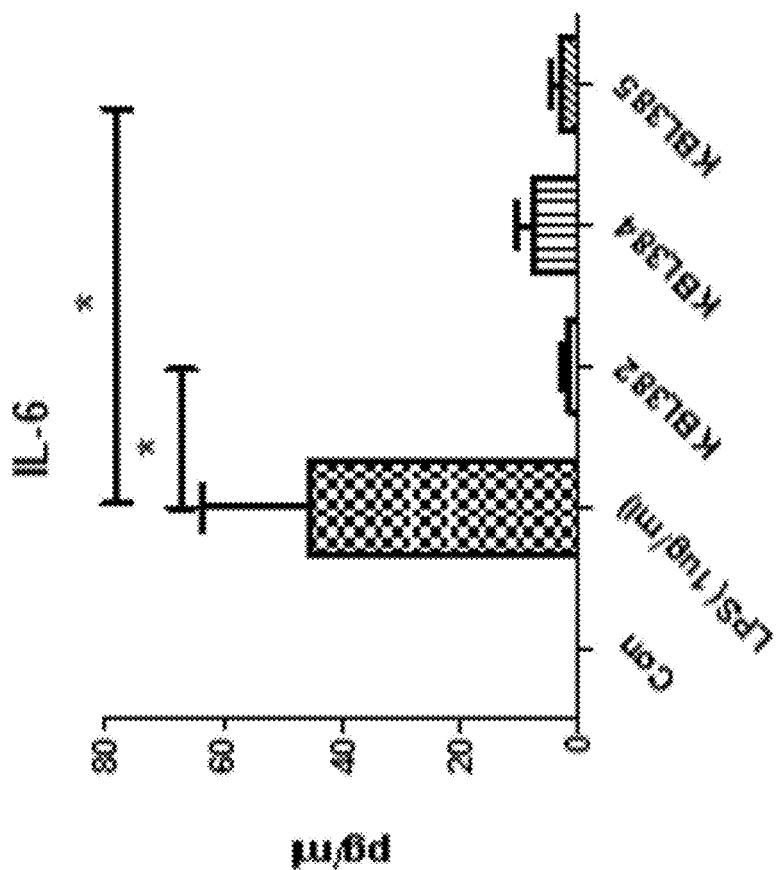
Figure 1E:
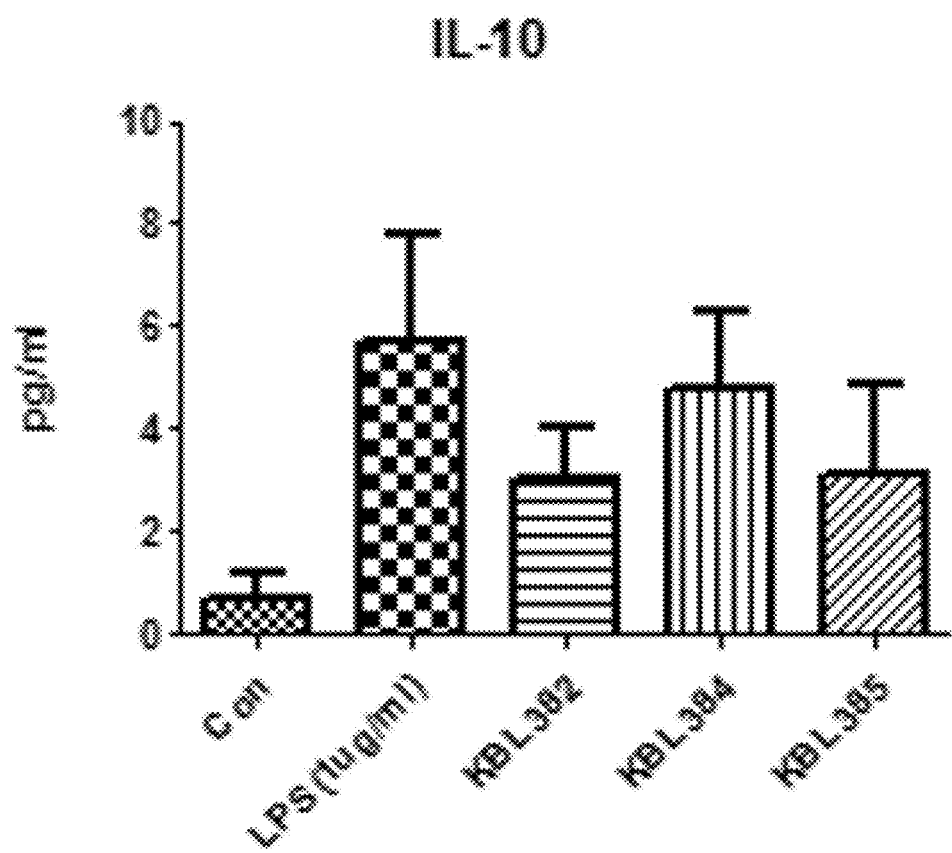
Figure 2B:
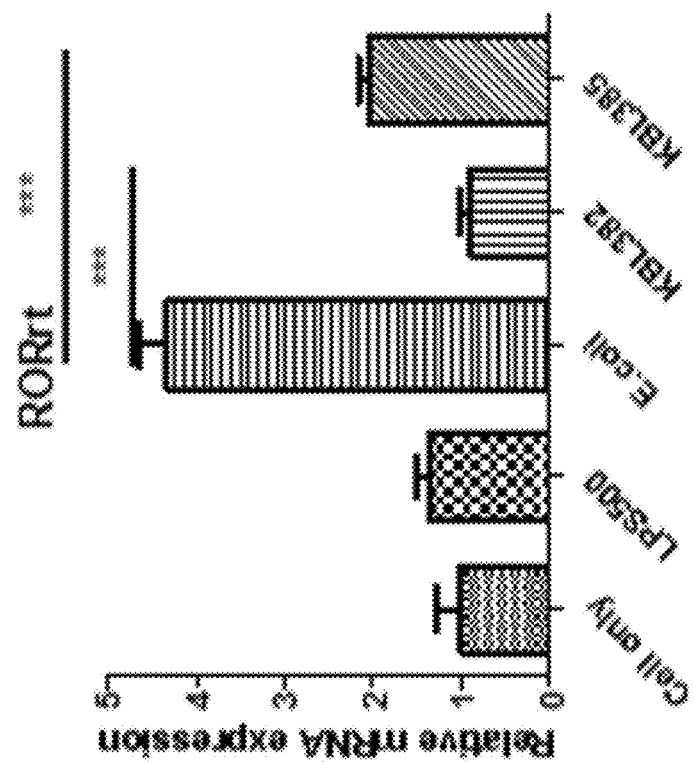
FIGS. 2A-2D illustrate the results confirming the effect of controlling gene expression of T cell differentiation markers by a KBL382 strain, a KBL384 strain and a KBL385 strain of the present invention in PBMC.
Figure 2A:
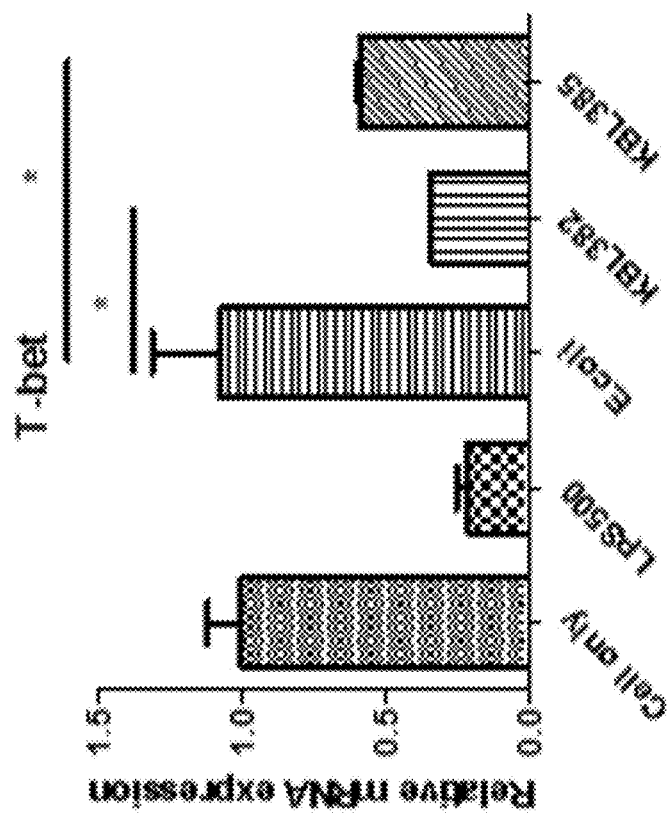
Figure 2C:
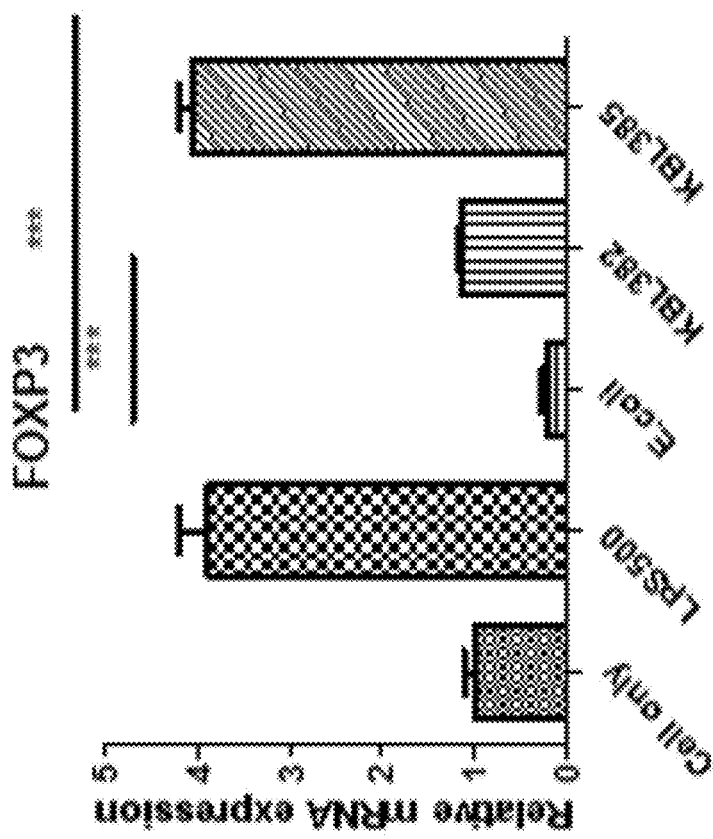
Figure 2D:
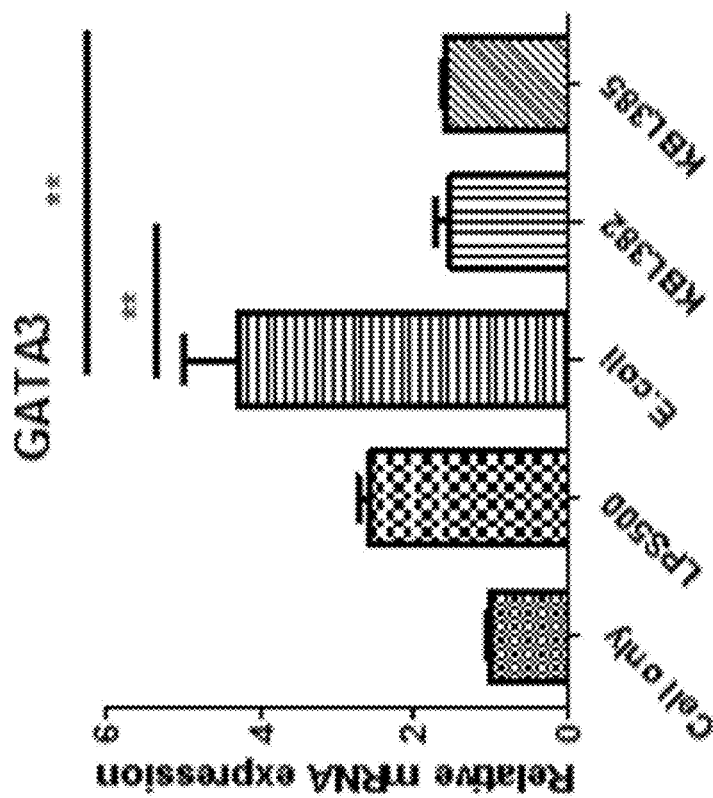
Figure 3A:
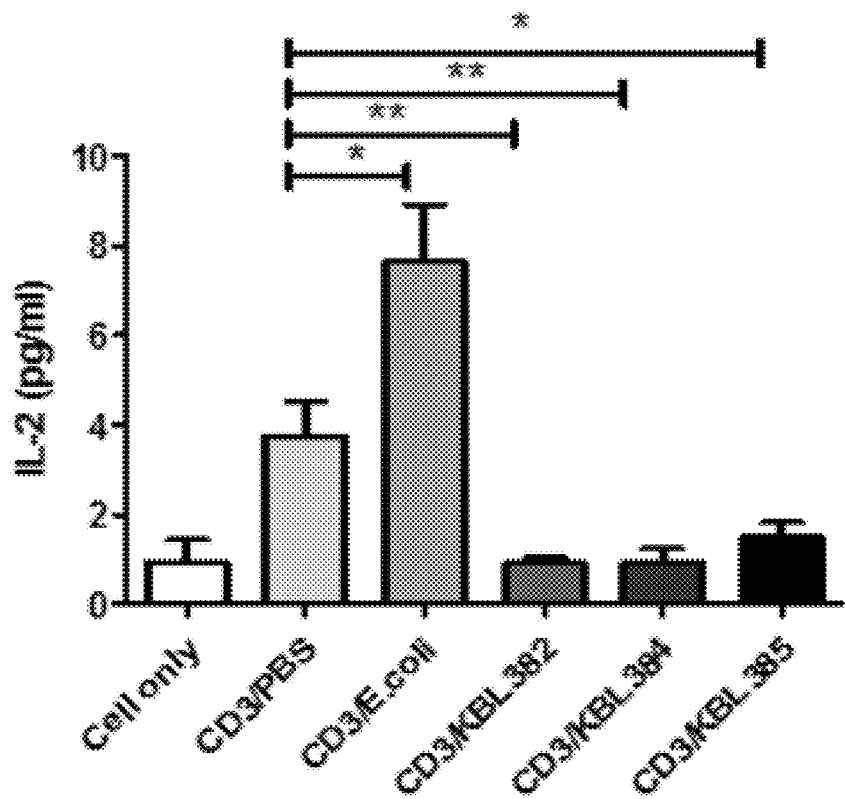
FIGS. 3A-3F illustrate the results of observing the change in expression level of cytokines, (FIG. 3A) IL-2, (FIG. 3B) IFN-$\gamma$, (FIG. 3C) IL-4, (FIG. 3D) IL-13, (FIG. 3E) IL-17A and (FIG. 3F) IL-10, according to the administration of a KBL382 strain, a KBL384 strain and a KBL385 strain of the present invention, in PBMC cell lines that T-cells are activated by addition of anti CD3 antibody.
Figure 3B:
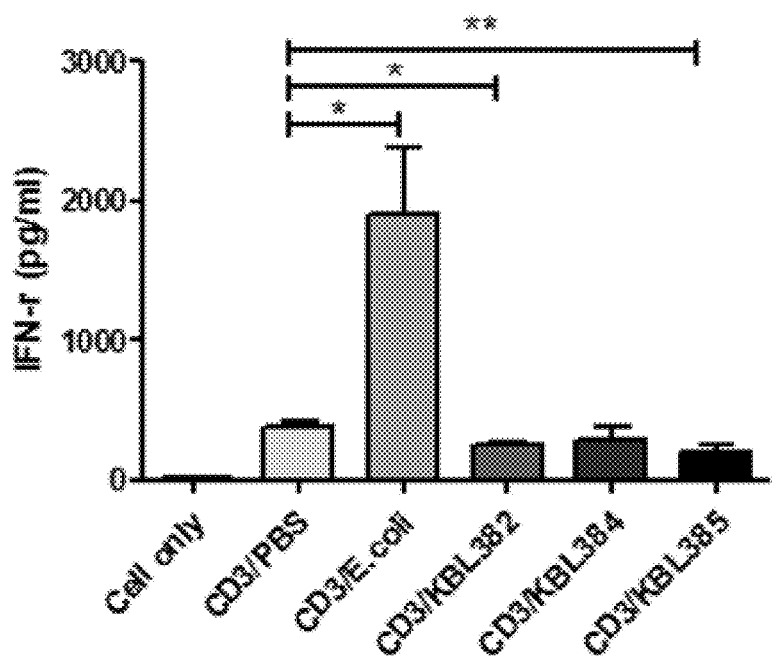
Figure 3C:
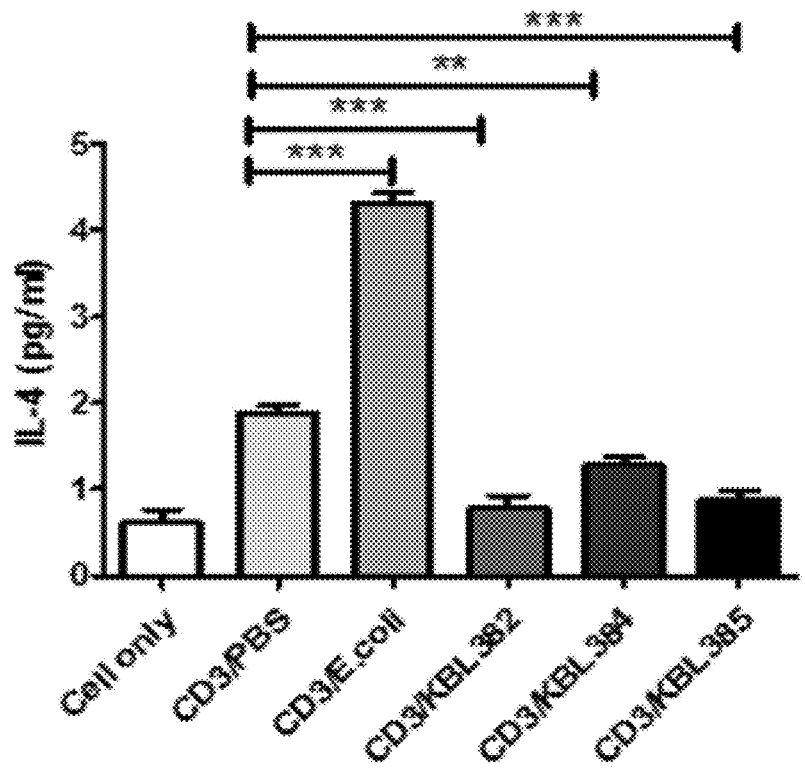
Figure 3D:
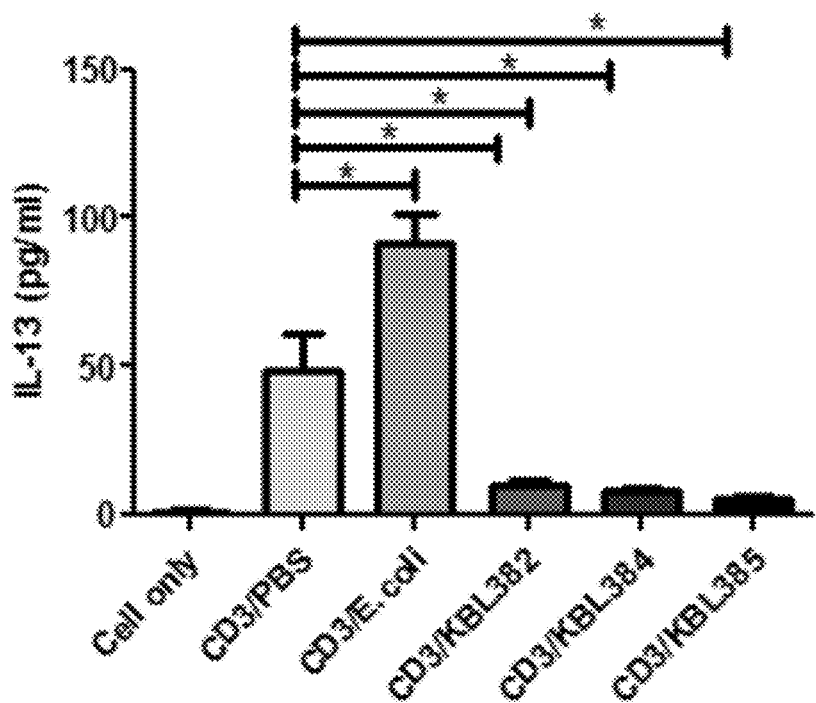
Figure 3E:
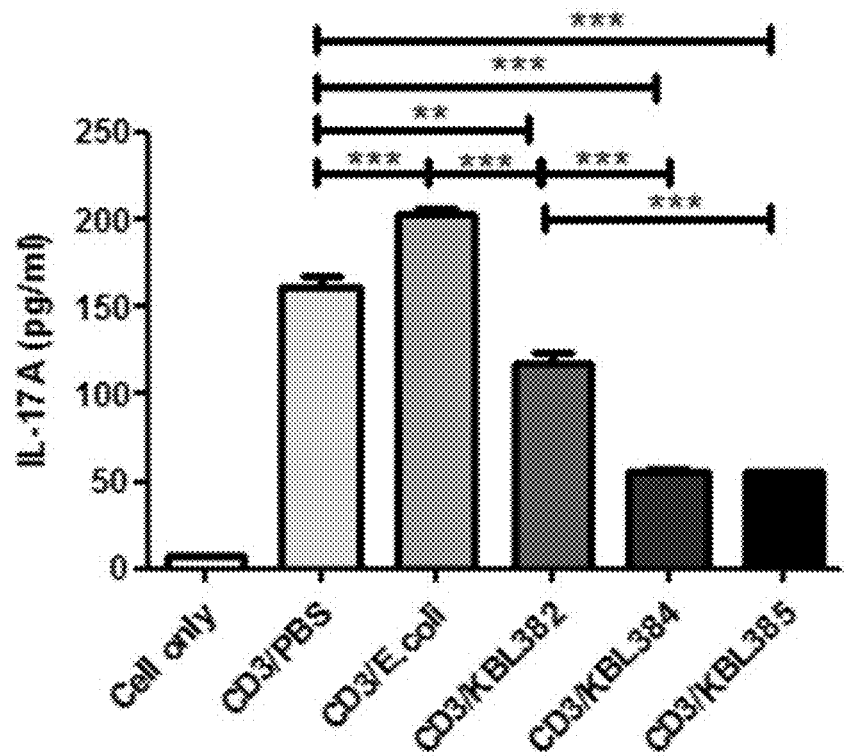
Figure 3F:
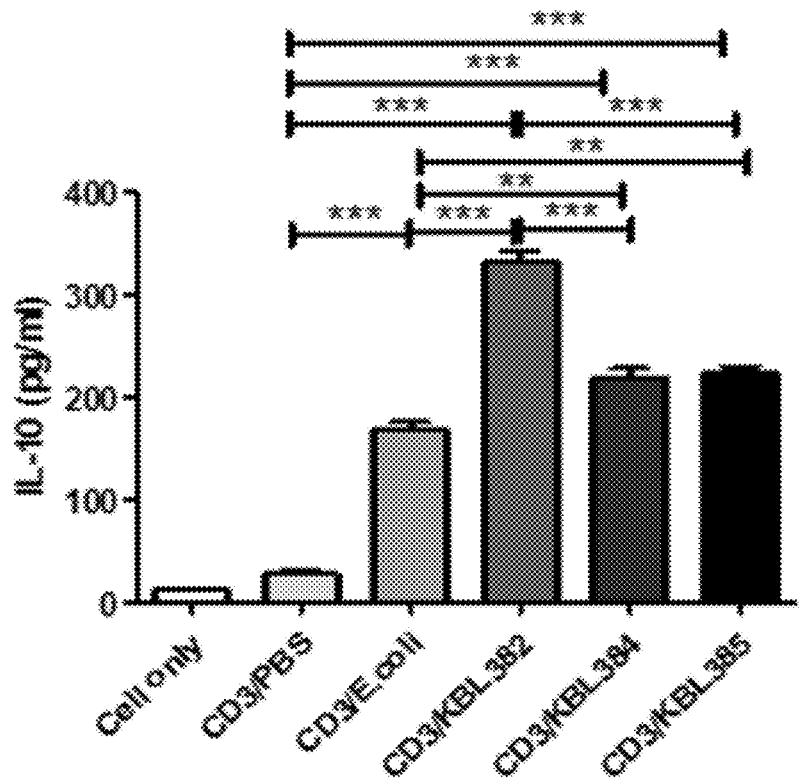
Figure 4A:
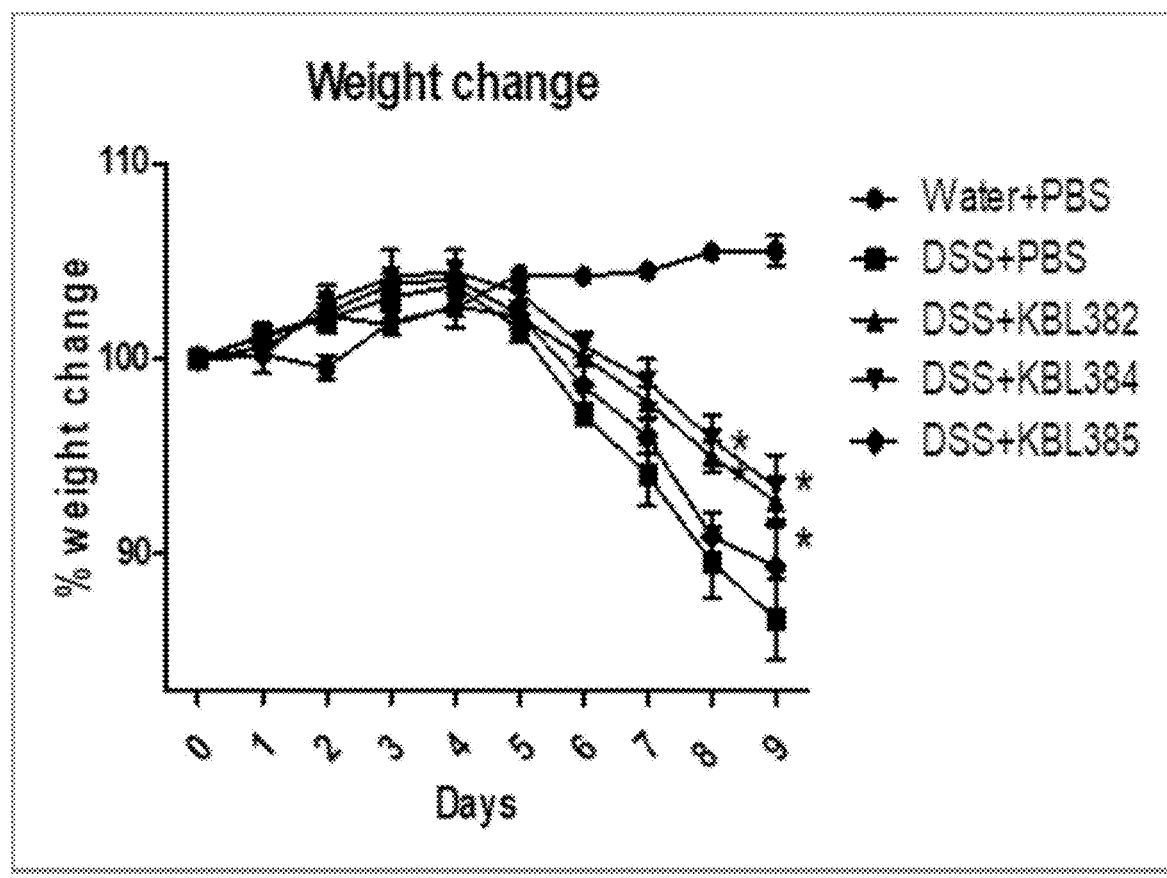
FIGS. 4A-4H illustrate the result confirming effects on alleviating enteritis through (FIG. 4A) body weight change, (FIG. 4B-4D) the colon length change, (FIG. 4E-4F) the colon length change and cecum weight change, (FIG. 4G) H&E staining of colon tissues and (FIG. 4H) the change in the MPO (myeloperoxidase) level in the colon tissues after administering each of a KBL382 strain, a KBL384 strain and a KBL385 strain of the present invention to mouse models that enteritis was induced.
Figure 4B:
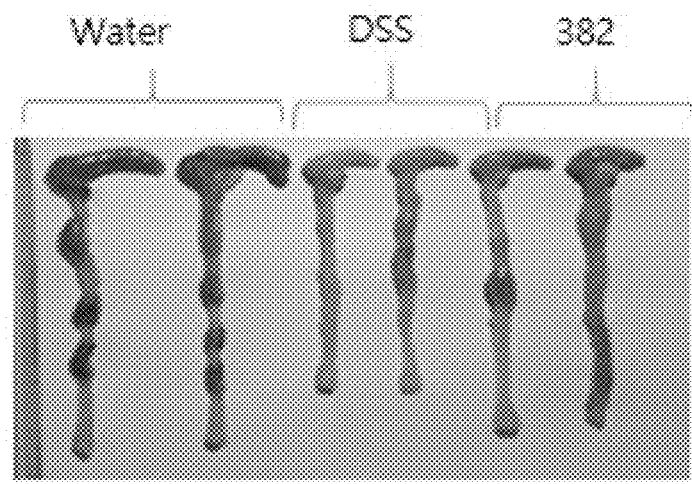
Figure 4C:
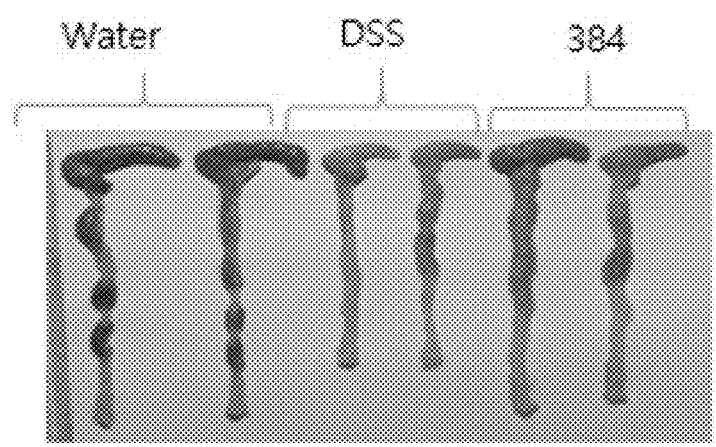
Figure 4D:
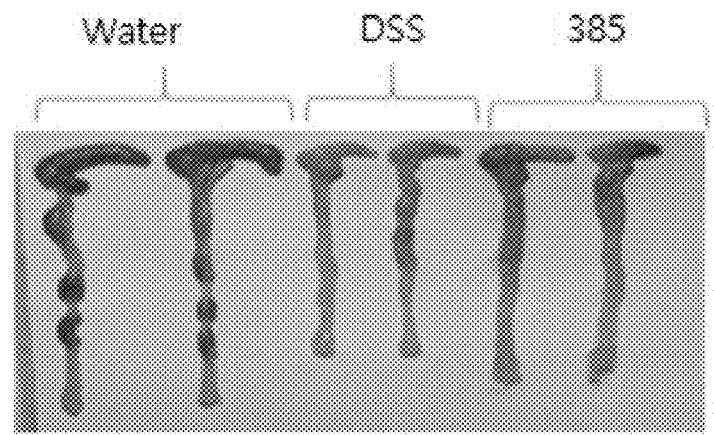
Figure 4E:
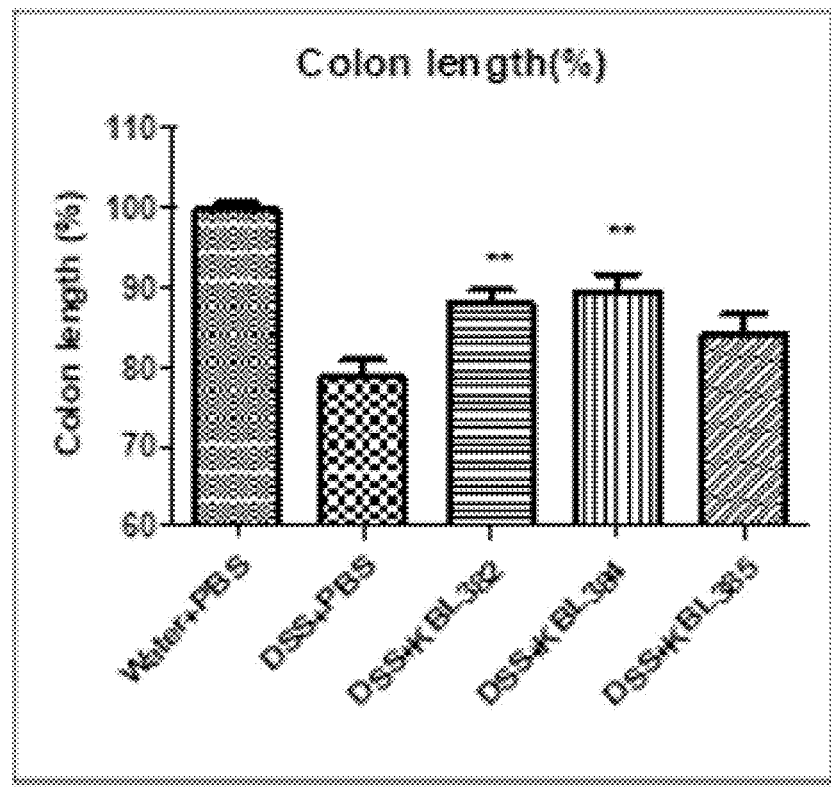
Figure 4F:
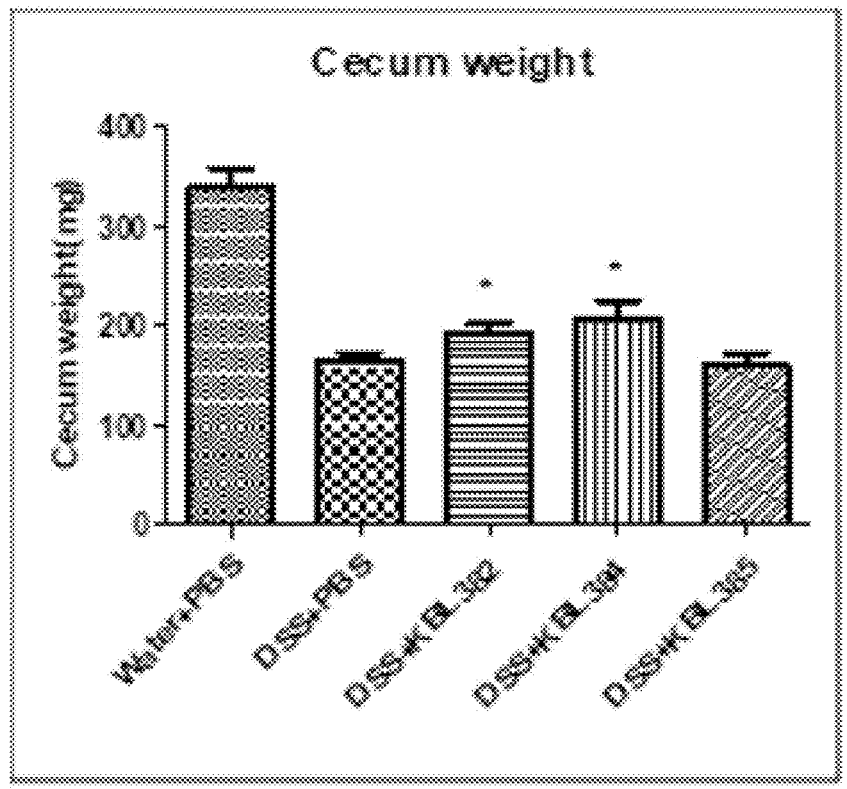
Figure 4G:
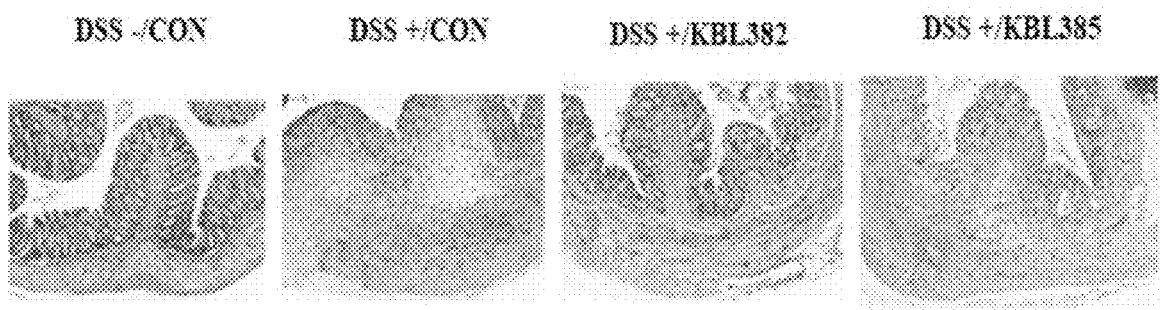
Figure 4H:
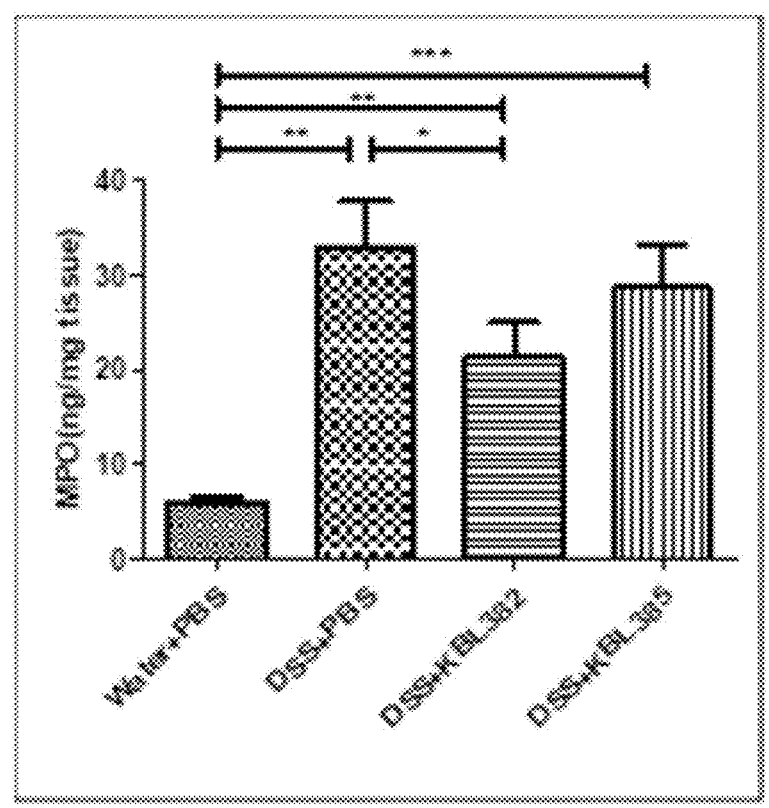

Unless defined otherwise, all of the technical, scientific terms used in the present specification mean the same as understood by a person having ordinary skills in the art ("those skilled in the art"). In general, the nomenclature used in the present specification is well known in the art and commonly used.

The present invention has confirmed an immunoregulatory effect of microorganisms derived from the human body, and found *Lactobacillus paracasei* strains having an excellent immunoregulation effect, i.e., KBL382 (Accession No. KCTC13509BP), KBL384 (Accession No. KCTC13510BP) and KBL385 strain (Accession No. KCTC13511BP). Analysis of 16s rDNA of said strain demonstrates that said strain is a novel strain which has never been known to the public.

In one embodiment, the present invention relates to a novel probiotic strain of *Lactobacillus paracasei* KBL382, of *Lactobacillus paracasei* KBL384 or of *Lactobacillus paracasei* KBL385, and said strains are characterized by comprising 16s rDNA sequences of SEQ ID NOs: 1 to 3, respectively, as below.

<SEQ ID NO: 1>
16s rDNA sequence of a *Lactobacillus paracasei* KBL382 strain
>KBL382
GCAGGTGGCGGGTGCTATACATGCAGTCGACGAGTTCTCGTTGATGATCGGTGCTTGCACC
GAGATTCAACATGGAACGAGTGGCGGACGGGTGAGTAACACGTGGGTAACCTGCCCTTAA
GTGGGGGATAACATTTGGAAACAGATGCTAATACCGCATAGATCCAAGAACCGCATGGTTC
TTGGCTGAAAGATGGCGTAAGCTATCGCTTTTGGATGGACCCGCGGCGTATTAGCTAGTTG
GTGAGGTAATGGCTCACCAAGGCGATGATACGTAGCCGAACTGAGAGGTTGATCGGCCAC
ATTGGGACTGAGACACGGCCCAAACTCCTACGGGAGGCAGCAGTAGGGAATCTTCCACAA
TGGACGCAAGTCTGATGGAGCAACGCCGCGTGAGTGAAGAAGGCTTTCGGGTCGTAAAAC
TCTGTTGTTGGAGAAGAATGGTCGGCAGAGTAACTGTTGTCGGCGTGACGGTATCCAACCA
GAAAGCCACGGCTAACTACGTGCCAGCAGCCGCGGTAATACGTAGGTGGCAAGCGTTATC
CGGATTTATTGGGCGTAAAGCGAGCGCAGGCGGTTTTTTAAGTCTGATGTGAAAGCCCTCG
GCTTAACCGAGGAAGCGCATCGGAAACTGGGAAACTTGAGTGCAGAAGAGGACAGTGGA
ACTCCATGTGTAGCGGTGAAATGCGTAGATATATGGAAGAACACCAGTGGCGAAGGCGGC
TGTCTGGTCTGTAACTGACGCTGAGGCTCGAAAGCATGGGTAGCGAACAGGATTAGATACC
CTGGTAGTCCATGCCGTAAACGATGAATGCTAGGTGTTGGAGGGTTTCCGCCCTTCAGTGC
CGCAGCTAACGCATTAAGCATTCCGCCTGGGGAGTACGACCGCAAGGTTGAAACTCAAAG
GAATTGACGGGGGCCCGCACAAGCGGTGGAGCATGTGGTTTAATTCGAAGCAACGCGAAG
AACCTTACCAGGTCTTGACATCTTTTGATCACCTGAGAGATCAGGTTTCCCCTTCGGGGGCA
AAATGACAGGTGGTGCATGGTTGTCGTCAGCTCGTGTCGTGAGATGTTGGGTTAAGTCCCG
CAACGAGCGCAACCCTTATGACTAGTTGCCAGCATTTAGTTGGGCACTCTAGTAAGACTGC
CGGTGACAAACCGGAGGAAGGTGGGGATGACGTCAAATCATCATGCCCCTTATGACCTGG
GCTACACACGTGCTACAATGGATGGTACAACGAGTTGCGAGACCGCGAGGTCAAGCTAAT
CTCTTAAAGCCATTCTCAGTTCGGACTGTAGGCTGCAACTCGCCTACACGAAGTCGGAATC
GCTAGTAATCGCGGATCAGCACGCCGCGGTGAATACGTTCCCGGGCCTTGTACACACCGC
CCGTCACACCATGAGAGTTTGTAACACCCGAAGCCGGTGGCGTAACCCTTTAGGGAGCGA
GCGTCTAAGTGGCTCACGCCT <SEQ ID NO: 2>
16s rDNA sequence of a *Lactobacillus paracasei* KBL384 strain
>KBL384
GCCAGTGGGGGGGGTGCTATACATGCAGTCGAACGAGTTCTCGTTGATGATCGGTGCTTGC
ACCGAGATTCAACATGGAACGAGTGGCGGACGGGTGAGTAACACGTGGGTAACCTGCCCT
TAAGTGGGGGATAACATTTGGAAACAGATGCTAATACCGCATAGATCCAAGAACCGCATG
GTTCTTGGCTGAAAGATGGCGTAAGCTATCGCTTTTGGATGGACCCGCGGCGTATTAGCTA
GTTGGTGAGGTAATGGCTCACCAAGGCGATGATACGTAGCCGAACTGAGAGGTTGATCGG
CCACATTGGGACTGAGACACGGCCCAAACTCCTACGGGAGGCAGCAGTAGGGAATCTTCC
ACAATGGACGCAAGTCTGATGGAGCAACGCCGCGTGAGTGAAGAAGGCTTTCGGGTCGTA
AAACTCTGTTGTTGGAGAAGAATGGTCGGCAGAGTAACTGTTGTCGGCGTGACGGTATCCA
ACCAGAAAGCCACGGCTAACTACGTGCCAGCAGCCGCGGTAATACGTAGGTGGCAAGCGT
TATCCGGATTTATTGGGCGTAAAGCGAGCGCAGGCGGTTTTTTAAGTCTGATGTGAAAGCC
CTCGGCTTAACCGAGGAAGCGCATCGGAAACTGGGAAACTTGAGTGCAGAAGAGGACAGT
GGAACTCCATGTGTAGCGGTGAAATGCGTAGATATATGGAAGAACACCAGTGGCGAAGGC -continued

```
GGCTGTCTGGTCTGTAACTGACGCTGAGGCTCGAAAGCATGGGTAGCGAACAGGATTAGA

TACCCTGGTAGTCCATGCCGTAAACGATGAATGCTAGGTGTTGGAGGGTTTCCGCCCTTCA

GTGCCGCAGCTAACGCATTAAGCATTCCGCCTGGGGAGTACGACCGCAAGGTTGAAACTC

AAAGGAATTGACGGGGGCCCGCACAAGCGGTGGAGCATGTGGTTTAATTGGAAGCAACGC

GAAGAACCTTACCAGGTCTTGACATCTTTTGATCACCTGAGAGATCAGGTTTCCCCTTCGGG

GGCAAAATGACAGGTGGTGCATGGTTGTCGTCAGCTCGTGTCGTGAGATGTTGGGTTAAGT

CCCGCAACGAGCGCAACCCTTATGACTAGTTGCCAGCATTTAGTTGGGCACTCTAGTAAGA

CTGCCGGTGACAAACCGGAGGAAGGTGGGGATGACGTCAAATCATCATGCCCCTTATGAC

CTGGGCTACACACGTGCTACAATGGATGGTACAACGAGTTGCGAGACCGCGAGGTCAAGC

TAATCTCTTAAAGCCATTCTCAGTTCGGACTGTAGGCTGCAACTCGCCTACACGAAGTCGGA

ATCGCTAGTAATCGCGGATCAGCACGCCGCGGTGAATACGTTCCCGGGCCTTGTACACACC

GCCCGTCACACCATGAGAGTTTGTAACACCCGAAGCCGGTGGCGTAACCCTTTAGGGAGC

GAGCGTCTAAGGTGAACCAAAGTTTG
```

<SEQ ID NO: 3>
16s rDNA sequence of a *Lactobacillus paracasei* KBL385 strain
>KBL385

```
GCAGTTGGGGGGGAGCTATACATGCAGTCGACGAGTTCTCGTTGATGATCGGTGCTTGCAC

CGAGATTCAACATGGAACGAGTGGCGGACGGGTGAGTAACACGTGGGTAACCTGCCCTTA

AGTGGGGGATAACATTTGGAAACAGATGCTAATACCGCATAGATCCAAGAACCGCATGGTT

CTTGGCTGAAAGATGGCGTAAGCTATCGCTTTTGGATGGACCCGCGGCGTATTAGCTAGTT

GGTGAGGTAATGGCTCACCAAGGCGATGATACGTAGCCGAACTGAGAGGTTGATCGGCCA

CATTGGGACTGAGACACGGCCCAAACTCCTACGGGAGGCAGCAGTAGGGAATCTTCCACA

ATGGACGCAAGTCTGATGGAGCAACGCCGCGTGAGTGAAGAAGGCTTTCGGGTCGTAAAA

CTCTGTTGTTGGAGAAGAATGGTCGGCAGAGTAACTGTTGCCGGCGTGACGGTATCCAACC

AGAAAGCCACGGCTAACTACGTGCCAGCAGCCGCGGTAATACGTAGGTGGCAAGCGTTAT

CCGGATTTATTGGGCGTAAAGCGAGCGCAGGCGGTTTTTTAAGTCTGATGTGAAAGCCCTC

GGCTTAACCGAGGAAGCGCATCGGAAACTGGGAAACTTGAGTGCAGAAGAGGACAGTGG

AACTCCATGTGTAGCGGTGAAATGCGTAGATATATGGAAGAACACCAGTGGCGAAGGCGG

CTGTCTGGTCTGTAACTGACGCTGAGGCTCGAAAGCATGGGTAGCGAACAGGATTAGATAC

CCTGGTAGTCCATGCCGTAAACGATGAATGCTAGGTGTTGGAGGGTTTCCGCCCTTCAGTG

CCGCAGCTAACGCATTAAGCATTCCGCCTGGGGAGTACGACCGCAAGGTTGAAACTCAAA

GGAATTGACGGGGGCCCGCACAAGCGGTGGAGCATGTGGTTTAATTCGAAGCAACGCGAA

GAACCTTACCAGGTCTTGACATCTTTTGATCACCTGAGAGATCAGGTTTCCCCTTCGGGGGC

AAAATGACAGGTGGTGCATGGTTGTCGTCAGCTCGTGTCGTGAGATGTTGGGTTAAGTCCC

GCAACGAGCGCAACCCTTATGACTAGTTGCCAGCATTTAGTTGGGCACTCTAGTAAGACTG

CCGGTGACAAACCGGAGGAAGGTGGGGATGACGTCAAATCATCATGCCCCTTATGACCTG

GGCTACACACGTGCTACAATGGATGGTACAACGAGTTGCGAGACCGCGAGGTCAAGCTAA

TCTCTTAAAGCCATTCTCAGTTCGGACTGTAGGCTGCAACTCGCCTACACGAAGTCGGAATC

GCTAGTAATCGCGGATCAGCACGCCGCGGTGAATACGTTCCCGGGCCTTGTACACACCGC

CCGTCACACCATGAGAGTTTGTAACACCCGAAGCCGGTGGCGTAACCCTTTAGGGAGCGA

GCCGTCTAAGTGTACAAAGTT
```

The present invention also confirmed that a KBL382 strain, a KBL384 strain, and a KBL385 strain each have a strengthening effect on tight junction of the intestinal tract wall in addition to anti-inflammatory and immunoregulatory effects, and that the administration of a KBL382 strain, a KBL384 strain and a KBL385 strain to animal models that enteritis was induced remarkably alleviated the body weight loss and the colon length reduction due to enteritis. Further, it has also been confirmed that the administration of the KBL382 strain, among the above strains, to animal models that atopic dermatitis was induced remarkably improved the dermatitis score, alleviated itching symptoms, lowered the skin thickness and remarkably improved the IgE concentration-in-blood due to allergic reaction.

Accordingly, in another embodiment, the present invention relates to a food composition or food additive composition comprising an effective amount of at least one selected from the group consisting of microbial cells of a KBL382 strain, a KBL384 strain, or a KBL385 strain, cultures of said strain, lysates of said strain, and extracts of said strain.

Said food composition or food additive composition can be readily utilized as the food effective for improvement of intestinal health and prevention of intestinal diseases, for example, as main ingredients or minor ingredients of food, food additives, health functional food composition or functional beverages, but not limited thereto.

Said food composition or food additive composition can be readily utilized as the food effective for alleviation of allergic symptoms, for example, as main ingredients or minor ingredients of food, food additives, health functional food composition or functional beverages, but not limited thereto.

Further, said food composition or food additive composition can be readily utilized as the food effective for alleviation of autoimmune diseases or inflammatory diseases, for example, as main ingredients or minor ingredients of food, food additives, health functional food composition or functional beverages, but not limited thereto.

The term "food" refers to a natural or artificial product comprising at least one nutrient, and more preferably, refers to a product which became edible through certain processing, usually encompassing all of food, food additives, health functional food and functional beverages.

The food that may comprise the said food composition according to the present invention as an additive may include, for example, different types of food, beverages, chewing gum, tea, vitamin complex, and functional food. In addition, the food of the present invention includes special nutritional food (e.g., modified milk, infant/baby food), processed meat products, fish meat products, tofu, muk, noodles (e.g., ramen, Asian noodles), bakery products, health supplement food, seasoning products (e.g., soy sauce, soybean paste, red pepper paste, mixed paste), sauces, confectionery (e.g., snack foods), candies, chocolates, chewing gums, ice-creams, milk products (e.g., fermented milk, cheese), other processed food, Kim-chi, salted food (e.g., different types of Kim-chi, pickled food), beverages (e.g., fruit juice, vegetable juice, soy milk, fermented beverages), and natural seasonings (e.g., broth powder for ramen), but not limited thereto. Said food, beverages or food additives can be prepared in conventional manners.

The term "health functional food" is a group of food to which value is added so as for the function thereof to be exerted and expressed for the predetermined purpose by using physical, biochemical or bioengineering techniques thereto, or a processed food designed so as for the in-vivo adjustment functions of the relevant food composition such as rhythm adjustment in prophylaxis, prevention of disease and recovery from disease to be sufficiently expressed. Such functional food may comprise food supplement additives which are food-scientifically acceptable, and may additionally comprise suitable carriers, excipients and diluents, which are commonly used in the manufacturing thereof.

The term "functional beverages", as used in the present invention, collectively refer to the drink products to relieve thirst or to enjoy the taste. There is no particular limitation thereto, except comprising the composition for improvement or prevention of said intestinal disease symptoms as essential ingredients with indicated ratio, and various flavoring agents or natural carbohydrates may be contained therein as additional ingredients like in common beverages.

In addition to the above, the food comprising the food composition according to the present invention for improvement of said intestinal disease symptoms or the prevention thereof may contain various nutrients, vitamins, minerals (electrolyte), flavoring agents such as synthetic flavoring agents and natural flavoring agents, coloring agents and fillers (cheese, chocolate, etc.), pectic acid and salts thereof, alginic acid and salts thereof, organic acids, protective colloidal thickening agents, pH adjusting agents, stabilizing agents, preservatives, glycerin, alcohol, carbonizing agents as used in carbonated beverages and the like, and each of the above ingredients may be used alone or in combination with each other.

In the food comprising the food composition according to the present invention, the composition of the present invention may be comprised in an amount of 0.001% by weight to 100% by weight, and preferably 1% by weight to 99% by weight, based on the total weight of the food; in the case of beverages, it may be comprised at an amount of 0.001 g to 10 g, and preferably 0.01 g to 1 g, based on 100 mL. For long-term intake for the purpose of health and hygiene or for the purpose of health control, however, the amount may be below the above-mentioned range; and since the effective ingredients have no problem in terms of safety profile, they can be used at an amount above the range and they are not limited to the amount range mentioned above.

The food composition according to the present invention may comprise the KBL382 strain, KBL384 strain, or KBL385 strain alone or in combination with the acceptable carrier, or may be prepared in the form of the composition suitable for consumption by human or animals. That is, the composition may be added to the food which contains no probiotic bacteria or a couple of probiotic bacteria. For example, the microorganisms which can be used in combination with the strain according to the present invention in preparing the food of the present invention should be suitable for the consumption by human or animals, and have probiotic activities to inhibit pathogenic, harmful bacteria or to improve the balance of microorganisms in the mammalian intestinal tract, upon intake, but not limited thereto. Such probiotic microorganisms may include, for example, yeast such as *Saccharomyces, Candida, Pichia* and *Torulopsis*, fungi such as *Aspergillus, Rhizopus, Mucor,* and *Penicillium*, and bacteria belonging to the genus of *Lactobacillus, Bifidobacterium, Leuconostoc, Lactococcus, Bacillus, Streptococcus, Propionibacterium, Enterococcus,* and *Pediococcus*. Suitable probiotic microorganisms specifically may include, for example, *Saccharomyces cerevisiae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus del-*

*bruckii, Lactobacillus johnsonii, Lactobacillus farciminus, Lactobacillus gasseri, Lactobacillus helveticus, Lactobacillus rhamnosus, Lactobacillus reuteri, Lactobacillus sakei, Lactococcus lactis,* or *Pediococcus acidilactici.* Preferably, the food composition according to the present invention may further comprise a probiotic microorganism mixture having excellent probiotic activities and superior effects on enhancing immunity to further enhance the effects thereof. The carriers that can be included in the food composition of the present invention may include, for example, extenders, high fiber additives, encapsulating agents, and lipids, which are widely well known in the art. The strain of *Lactobacillus paracasei* in the present invention may be in the lyophilized or encapsulated form or in the form of culture suspensions or dry powders.

The composition of the present invention can also be provided in the form of a feed additive comprising said strain or a feed comprising the same.

The feed additive of the present invention may be in the form of dry or liquid formulation, and further comprise other non-pathogenic microorganisms in addition to the said strain of KBL382, KBL384, or KBL385. The microorganisms that can be added to the feed additive may include, for example, *Bacillus subtilis* that can produce protease, lipase and sugar-converting enzymes, *Lactobacillus* strain having a physiological activity and degradability of organic compounds under anaerobic conditions such as in the stomach of cow, filamentous fungi such as *Aspergillus oryzae* showing effects on increasing weight of livestock, milk yield, and digestibility of the feed (Slyter, L. L. J. Animal Sci. 1976, 43. 910-926) and yeast such as *Saccharomyces cerevisiae* (Johnson, D. E et al. J. Anim. Sci., 1983, 56, 735-739; Williams, P. E. V. et al, 1990, 211).

The feed additive of the present invention may additionally comprise at least one enzyme agent in addition to said *Lactobacillus paracasei* KBL382 strain, *Lactobacillus paracasei* KBL384 strain, or *Lactobacillus paracasei* KBL385 strain. The additional enzyme agents can be in a dry or liquid form, and may include, for example, steatolytic enzymes such as lipase, phytase to produce phosphate and inositol phosphate by degrading phytic acid, amylase, i.e., an enzyme to hydrolyze α-1,4-glycoside bond included in, for example, starch and glycogen, phosphatase, i.e., an enzyme to hydrolyze organic phosphoric acid ester, carboxymethylcellulase to degrade cellulose, xylase to degrade xylose, maltase to hydrolyze maltose into two glucose molecules, and sugar producing enzymes such as invertase to produce glucose-fructose mixture by hydrolyzing saccharose.

In the use of the *Lactobacillus paracasei* KBL382 strain, *Lactobacillus paracasei* KBL384 strain, or *Lactobacillus paracasei* KBL385 strain of the present invention as feed additives, the raw ingredients for the feed, such as peanuts, peas, beets, pulp, grain by-products, animal guts powder and fish meal powder, including various grains and soybean protein, can be used. They may be processed or not, and can be used without limitation. The processing may include, but not limited thereto, such a process that the raw ingredients of the feed are charged and can be compressed under pressure against a given outlet, and for proteins, extrusion by which proteins are degenerated to increase availability may be preferably used. Extrusion has advantages of denaturing proteins through thermal treatment and destroying antien-zyme factors. Further, for soybean proteins, the digestibility thereof can be improved through extrusion to inactivate anti-nutrients such as a trypsin inhibitor, one of inhibitors of protease that are present in soybeans. Further, extrusion can promote improvement of digestibility by protease, enhancing the nutritional value of soybean proteins.

In another embodiment, the present invention relates to a pharmaceutical composition for the treatment or prevention of intestinal diseases, comprising an effective amount of at least one selected from the group consisting of microbial cells of a *Lactobacillus paracasei* KBL382 strain, a *Lactobacillus paracasei* KBL384 strain, or a *Lactobacillus paracasei* KBL385 strain, cultures of said strain, lysates of said strain, and extracts of said strain.

In another embodiment, the present invention relates to a pharmaceutical composition for the treatment or prevention of allergic diseases, comprising an effective amount of at least one selected from the group consisting of microbial cells of a *Lactobacillus paracasei* KBL382 strain, a *Lactobacillus paracasei* KBL384 strain, or a *Lactobacillus paracasei* KBL385 strain, cultures of said strain, lysates of said strain, and extracts of said strain.

In another embodiment, the present invention relates to a pharmaceutical composition for the treatment or prevention of autoimmune diseases or inflammatory diseases, comprising an effective amount of at least one selected from the group consisting of microbial cells of a *Lactobacillus paracasei* KBL382 strain, a *Lactobacillus paracasei* KBL384 strain, or a *Lactobacillus paracasei* KBL385 strain, cultures of said strain, lysates of said strain, and extracts of said strain.

The pharmaceutical composition of the present invention can be provided in a form of live bacteria, dry strain, cultures of said strain, lysates of said strain, or a composition in combination with a pharmaceutically acceptable carrier or media. The carriers or media that can be used herein may include solvent, a dispersant, a coating, an enhancer, a controlled-release formulation (i.e., sustained-release formulation), or at least one inert excipient including starch, polyol, granules, microfine cellulose, microcrystalline cellulose such as Celphere, Celphere beads, diluent, lubricant, binder, disintegrant, and the like. The tablet of the above composition may be, if desired, coated by a standard aqueous or non-aqueous technique. The examples of the pharmaceutically acceptable carrier and the excipient for the use as the pharmaceutically acceptable inert carrier, and said additional ingredients may include, for example, a binder, a filler, a disintegrant, a lubricant, an antimicrobial agent and a coating agent, but not limited thereto.

The present invention may be characterized in that said intestinal diseases are selected from the group consisting of abdominal bloating, abdominal discomfort, infectious diarrhea caused by pathogenic microorganisms, gastroenteritis, inflammatory bowel diseases, neurogenical intestinitis syndrome, irritable bowel syndrome, overgrowth of small intestinal microorganisms and intestinal feeding diarrhea, and the diseases also include those caused by damage of barrier function of intestine.

The inflammatory bowel disease (IBD) may include Crohn's disease, the intestinal lesion accompanying with Behcet's disease, ulcerative colitis, hemorrhagic rectal ulcer, and pouchitis, and refers to a group of diseases including Crohn's disease and ulcerative colitis. Ulcerative colitis only affects the colon. Inflammation and ulcer of ulcerative colitis are limited to the two innermost layers, mucosa and submucosa out of four layers of the colon. Inflammation and ulcer of Crohn's disease can be spread throughout all layers of the intestinal wall in both small and large intestine.

Meanwhile, the irritable bowel syndrome is a chronic condition accompanying not only persistently recurrent abdominal discomfort and pain such as abdominal bloating, but also changes in bowel habit such as diarrhea and constipation. The symptoms may be exacerbated by psychological factors or stressful social circumstances.

In the present invention, the allergic diseases may include atopic dermatitis, urticaria, allergic rhinitis, allergic conjunctivitis, asthma, food allergy and anaphylactic shock, but not limited thereto.

In the present invention, autoimmune diseases may include, for example, rheumatoid arthritis, lupus, systemic scleroderma, atopic dermatitis, psoriasis, psoriatic arthritis, asthma, Guilian-Barre syndrome, myasthenia gravis, dermatomyositis, polymyositis, multiple sclerosis, autoimmune encephalomyelitis, polyarteritis nodosa, Hashimoto's thyroiditis, multiple sclerosis, temporal arteritis, juvenile diabetes, alopecia areata, pemphigus, aphthous stomatitis, autoimmune hemolytic anemia, Wegener's granulomatosis, Sjogren's syndrome, Addison's disease, Crohn's disease, and Behcet's disease, but not limited thereto.

Further, inflammatory diseases of the present invention collectively refer to conditions having inflammation as a main lesion, and may include, for example, edema, conjunctivitis, periodontitis, rhinitis, otitis media, chronic sinusitis, pharyngolaryngitis, tonsillitis, bronchitis, pneumonia, gastric ulcer, gastritis, colitis, gout, eczema, acne, atopic dermatitis, contact dermatitis, seborrheic dermatitis, ankylosing spondylitis, rheumatic fever, fibromyalgia, osteoarthritis, psoriatic arthritis, rheumatoid arthritis, peri-arthritis of the shoulder, tendinitis, tenosynovitis myositis, hepatitis, cystitis, nephritis, Sjogren's syndrome, myasthenia gravis, sepsis, vasculitis, bursitis, temporal arteritis, and multiple sclerosis, but not limited thereto.

It is known that autoimmune diseases can be prevented or treated by an activation of regulatory T cells (Treg) or differentiation into T cells. Treg, a type of CD4+ T cell, plays a role in regulating the immune system and controlling autoimmune diseases by maintaining tolerance to autoantigens. A transcription factor called Foxp3 is specifically involved in the development, maintenance, and function of regulatory T cells, regulating the immune response through the secretion of the immunosuppressive cytokines IL-10 and TGF-$\beta$.

In addition, it is known that when the differentiation rate of T cells into Th1 cells, Th2 cells, and Th17 cells is low and the differentiation rate of T cells into Treg cells is high, the inflammatory response can be effectively suppressed.

Th1 cells, Th2 cells and Th17 cells differentiated from splenic T cells are known to be associated with the expression of the following transcription factors and cytokines: In the case of Th1 cells, T-bet, IFN-$\gamma$ and IL-12; in the case of Th2 cells, GATA3 and IL-5; in the case of Th17 cells, ROR$\gamma$t, IL-17.

The present invention may be characterized in that the effects resulting from the strain of the present invention for alleviating, treating or preventing autoimmune diseases or inflammatory diseases can be induced by at least one selected from the following mechanisms:

i) suppression of expression or secretion of at least one selected from the group consisting of the inflammatory cytokines IL-6, TNF, IL-1b, IL-8, IL-2, IFN-$\gamma$, IL-4, IL-13, and IL-17A;

ii) increase of expression or secretion of the anti-inflammatory and immunoregulatory cytokine IL-10; and iii) increase of expression of Treg involved in anti-inflammatory activities and immunoregulation.

The term 'treating', unless mentioned otherwise, refers to reversing or alleviating the diseases or conditions used with said term or one or more symptoms thereof, inhibiting the progression of the same or preventing the same. The term 'treatment' as used in the present invention refers to an act of 'treating' as defined above. Accordingly, treatment or therapeutic regimen of intestinal diseases, allergic diseases, autoimmune diseases or inflammatory diseases in mammals may include one or more of the following:

(1) Inhibit the development of intestinal diseases, allergic diseases, autoimmune diseases or inflammatory diseases, (2) Prevent the spread of the intestinal diseases, allergic diseases, autoimmune diseases or inflammatory diseases, (3) Alleviate the intestinal diseases, allergic diseases, autoimmune diseases or inflammatory diseases, (4) Prevent recurrence of the intestinal diseases, allergic diseases, autoimmune diseases or inflammatory diseases, and (5) Palliate the symptoms of the intestinal diseases, allergic diseases, autoimmune diseases or inflammatory diseases A composition of the present invention for preventing or treating intestinal diseases, allergic diseases, autoimmune diseases or inflammatory diseases may comprise a pharmaceutically effective amount of a *Lactobacillus paracasei* KBL382 strain, a *Lactobacillus paracasei* KBL384 strain, a *Lactobacillus paracasei* KBL385 strain alone or in combination with at least one of pharmaceutically acceptable carriers, excipients or diluents.

In the present invention, the term "effective amount" means an amount that is high enough to provide a desired effect but is low enough to prevent serious side effects under medical judgment. The amount of microorganisms administered to the body by the composition of the present invention can be appropriately adjusted in consideration of the administration route and the administration target.

The composition of the present invention can be administered to a subject once or more per day. Unit dosage means physically discrete units suitable for unit administration to human subjects and other mammals, and each unit comprises a suitable pharmaceutical carrier and a predetermined amount of the microorganisms of the present invention to provide a therapeutic effect. The dosage unit for oral administration to an adult patient preferably contains 0.001 g or more of the microorganism of the present invention, and the oral dosage of the composition of the present invention is from 0.001 g to 10 g, and preferably from 0.01 g to 5 g per dose. The pharmaceutically effective amount of the microorganism of the present invention is from 0.01 g to 10 g/day. However, the dosage varies depending on the severity of the patient's disease and the microorganisms and auxiliary effective ingredients used together. In addition, the total daily dosage can be divided into several times and continuously administered as needed. Accordingly, the above dosage ranges do not limit the scope of the present invention in any way.

Further, the term "pharmaceutically acceptable" as used above refers to a composition that is physiologically acceptable and does not cause an allergic reaction such as gastrointestinal disorder, dizziness, or similar reaction when administered to a human.

A composition of the present invention can be formulated using methods known in the art so that rapid, sustained or delayed release of the active ingredients, after administered to a mammal, can be provided. The dosage forms may be powders, granules, tablets, emulsions, syrups, aerosols, soft or hard gelatin capsules, sterile injection solutions, or sterile powders. Further, the composition of the present invention for preventing or treating intestinal diseases can be administered via several routes, including oral, transdermal, subcutaneous, intravenous or intramuscular administration. The dosage of the active ingredients can be appropriately selected depending on various factors such as the route of administration, the patient's age, sex, weight, and the severity of the patient. The composition of the present invention for preventing or treating gastrointestinal diseases can be administered in combination with a known compound having the effect of preventing or treating the symptoms of intestinal diseases.

The pharmaceutical composition of the present invention, in particular, can be provided in an oral unit dosage form of an enteric coated formulation. The term "enteric coating", as used herein, comprises any known pharmaceutically acceptable coating which can remain in the stomach without degrading by the gastric acid and can sufficiently disintegrate in the intestinal tract to release active ingredients therein. The "enteric coating" of the present invention refers to a coating that can be maintained for 2 hours or more when an artificial gastric juice such as an HCl solution of pH 1 is contacted thereto at 36° C. to 38° C., and subsequently can degrade, preferably in an artificial intestinal juice such as a $KH_2PO_4$ buffer solution of pH 6.8 in 30 minutes.

The enteric coating of the present invention is coated on one core in an amount of from about 16 mg to 30 mg, preferably from 16 mg to 20 mg or 25 mg or less. When the thickness of the enteric coating of the present invention is 5 μm to 100 μm, and preferably 20 μm to 80 μm, satisfactory results can be obtained as an enteric coating. The material of the enteric coating can be suitably selected from known polymeric materials. Suitable polymeric materials are listed in a number of known documents (L. Lachman et al., The Theory and Practice of Industrial Pharmacy, $3^{rd}$ ed., 1986, pp. 365-373; H. Sucker et al., Pharmazeutische Technologie, Thieme, 1991, pp. 355-359; Hagers Handbuchder pharmazeutischen Praxis, $4^{th}$ ed., Vol. 7, pp. 739-742, and 766-778, (SpringerVerlag, 1971); and Remington's Pharmaceutical Sciences, $13^{th}$ ed., pp. 1689-1691 (Mack Publ., Co., 1970)), and cellulose ester derivatives, cellulose ethers, a copolymer of acrylic resin and methylacrylate, and a copolymer of maleic acid and phthalic acid derivatives can be included therein.

The enteric coating of the present invention can be prepared using a conventional enteric coating method in which an enteric coating solution is sprayed onto a core. Suitable solvents used for the enteric coating process are alcohols such as ethanol, ketones such as acetone, halogenated hydrocarbon solvents such as dichloromethane ($CH2Cl_2$), and mixed solvents of these solvents. A softener such as di-n-butyl phthalate or triacetin is added to the coating solution in a ratio of 1:about 0.05 to about 0.3 (coating material:softener). It is appropriate to carry out the spraying process continuously, and it is possible to adjust the spraying amount in consideration of the conditions of coating. The spraying pressure can be variously adjusted, and satisfactory results can be obtained generally with a spraying pressure of about 1 bar to about 1.5 bar.

In another embodiment, the present invention relates to the use of said strain or composition for the prevention or treatment of intestinal diseases, allergic diseases, autoimmune diseases or inflammatory diseases, and the use of said strain or composition for preparing a therapeutic agent for intestinal diseases, allergic diseases, autoimmune diseases or inflammatory diseases.

Specifically, the present invention relates to a composition for the use of preventing or treating intestinal diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

In addition, the present invention relates to a composition for the use of preventing or treating allergic diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

In addition, the present invention relates to a composition for the use of preventing or treating autoimmune diseases or inflammatory diseases, comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain.

The present invention also relates to the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain, for preparing a preventive or therapeutic drug for intestinal diseases.

In addition, the present invention relates to the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain, for preparing a preventive or therapeutic drug for allergic diseases.

In addition, the present invention relates to the use of a composition comprising at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain, for preparing a preventive or therapeutic drug for autoimmune diseases or inflammatory diseases.

The term 'prevention', as used herein, is associated with averting, delaying, impeding or hindering diseases to reduce the same.

The term 'treatment', as used herein, is associated with caring for a subject suffering from diseases in order to ameliorate, cure or reduce the symptoms of the diseases or to reduce or stop the progression of the diseases.

In another embodiment, the present invention provides a method for preventing or treating intestinal diseases, allergic diseases, autoimmune diseases or inflammatory diseases, comprising administering a pharmaceutically effective amount of said strain or said composition to a subject in need of prevention or treatment of said diseases, or in need of alleviation of the intestinal health, allergic reactions, decreased level of immunity or inflammatory reactions.

Specifically, the present invention provides a method for treating intestinal diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain to a subject in need thereof.

In addition, the present invention provides a method for treating allergic diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain to a subject in need thereof.

In addition, the present invention provides a method for treating autoimmune diseases or inflammatory diseases, comprising administering a therapeutically effective amount of at least one selected from the group consisting of a *Lactobacillus paracasei* KBL382 strain (Accession No. KCTC13509BP), a *Lactobacillus paracasei* KBL384 strain (Accession No. KCTC13510BP), or a *Lactobacillus paracasei* KBL385 strain (Accession No. KCTC13511BP), cultures of said strain, lysates of said strain, and extracts of said strain to a subject in need thereof.

Since the pharmaceutical composition used for the method for preventing or treating said intestinal diseases, allergic diseases, autoimmune diseases or inflammatory diseases, and the administration method thereof have been described above, the overlapping contents between the composition and the method will be omitted herein to avoid excessive complexity of the present specification.

Meanwhile, the said subject to which the composition for preventing or treating said intestinal diseases, allergic diseases, autoimmune diseases or inflammatory diseases can be administered includes all animals including human. For example, the subject may be an animal such as dog, cat, or mouse.

Hereinafter, the present invention will be described in more detail through examples. These examples are only for illustrating the present invention, and it will be apparent to those skilled in the art that the scope of the present invention is not to be construed as being limited by these examples.

Example 1. Screening of Probiotic Strains with Immunoregulatory Function

Probiotic strains having an immunoregulatory function were screened using the leukemia monocyte THP-1 cell line and peripheral blood mononuclear cells (PBMC). Strains derived from human gut or vagina, respectively, were seeded to the above two cell lines so that the ratio of cell line:strain was 1:100, and the ratio of IL-10, a major cytokine indicating inflammation control, to IL-6, a major cytokine indicating an inflammatory reaction (IL-10/IL-6), and the ratio of IL-10 to IFN-$\gamma$, a major cytokine indicating autoimmune reaction (IL-10/IFN-$\gamma$) were measured. A total of 23 strains were used for the screening as follows: two *Lactobacillus gasseri* strains, one *Lactobacillus reuteri* strain, five *Lactobacillus rhamnosus* strains, two *Lactobacillus fermentum* strains, four *Lactobacillus paracasei* strains, four *Lactobacillus salivarius* strains, one *Lactobacillus plantarum* strain, two *Lactobacillus acidophilus* strains and two *Lactococcus lactis* strains.

As a result of the screening, the highest IL-10/IL-6 values were shown in the three strains of *Lactobacillus paracasei* KBL382, KBL384 and KBL385. In particular, among the three *Lactobacillus paracasei* strains, KBL382 had the highest IL-10/IL-6 value of 2.22 in the THP-1 cell line, and the IL-10/IFN-$\gamma$ value was 9 in peripheral blood mononuclear cells, showing a very high immunoregulatory effect. Table 1 below shows the results of the IL-10/IL-6 value and IL-10/IFN-$\gamma$ value measured for three *Lactobacillus paracasei* strains out of the twenty three probiotic strains used in the present screening. Accordingly, three strains of *Lactobacillus paracasei* KBL382, KBL384 and KBL385 were predicted to have a high effect on improving intestinal health, and additional experiments were conducted on these strains.

TABLE 1

| Cell line | Strain | IL-10/IL-6 |
|---|---|---|
| THP-1 | *Lactobacillus paracasei* KBL382 | 2.222168 |
|  | *Lactobacillus paracasei* KBL384 | 0.621436 |
|  | *Lactobacillus paracasei* KBL385 | 1.08215 |
| Cell | Strain | IL-10/IFN-r |
| PBMC | *Lactobacillus paracasei* KBL382 | 9.0295403 |
|  | *Lactobacillus paracasei* KBL384 | 7.4016942 |
|  | *Lactobacillus paracasei* KBL385 | 7.9818579 |

Example 2. Verification of the Effect of *Lactobacillus paracasei* KBL382, KBL384 and KBL385 Strains on Inflammatory Cytokine Expression and T-Cell Differentiation Regulation (In Vitro Test)

In order to verify the immunoregulatory effect from said *Lactobacillus paracasei* KBL382, KBL384 and KBL385 strains, the ability to generate cytokines involved in immunoregulation was confirmed in THP-1 cell line treated with the *Lactobacillus paracasei* KBL382, KBL384 and KBL385 strains, while whether the marker gene of T-cell differentiation was expressed was confirmed in PBMC treated with the *Lactobacillus paracasei* KBL382 and KBL385 strains.

First, the THP-1 cell line was seeded onto each well of a 24-well plate by $1\times10^5$ cells, differentiated into mature macrophages, and then the culture solution was replaced. After 3 hours, one well was treated with LPS at a concentration of 1 μg/mL as a positive control, and the other wells were treated with the *Lactobacillus paracasei* KBL382, KBL384 or KBL385 strain, each by $1\times10^7$ cells based on the number of viable bacteria; after 24 hours, the culture solution was collected and the amount of each cytokine was measured using the BD Cytometric Bead Array (CBA) human inflammation kit (Cat No. 551811) according to the manufacturer's method. As a negative control (Cont), the well was treated with PBS buffer and the same experimental procedure was performed. As a result, as shown in FIGS. 1A-1E, the measurement showed that a group of THP-1 cell lines treated with *Lactobacillus paracasei* KBL382 and KBL385 strains had a significantly lower amount of inflammatory cytokines IL-6, TNF, IL-1b and IL-8 than the LPS-treated group. In the case of the treatment with the KBL384 strain, it was confirmed that IL-6 was significantly lower than the test group treated with LPS, but TNF, IL-1b and IL-8 were not different significantly from the group treated with LPS. In the case of IL-10, any significant increase or decrease was not observed in the groups treated with the KBL382, KBL384 and KBL385 as compared to the group treated with LPS, but it was observed that overall increase in IL-10 level was induced as compared to the negative control group. Therefore, it was concluded that *Lactobacillus paracasei* KBL382 and KBL385 strains were effective for significantly suppressing the generation of inflammatory cytokines in THP-1 cells, and the subsequent experiment was conducted to verify the pattern of T cell differentiation.

In order to confirm the effect of the KBL382 and KBL385 strains on T cell differentiation, PBMC cells were seeded onto each well of a 24-well plate by 5×10$^5$ cells, and then the *Lactobacillus paracasei* KBL382 or KBL385 strain was added by 5×10$^6$ cells. As a control, *E. coli* (*E. coli* 0157 EC4115) was added to each well by 5×10$^6$ cells based on the number of viable cells, or LPS was added at a concentration of 500 ng/mL. *E. coli* is known to increase the expression of T-bet, GATA3, and RORγt genes, which are effector cell markers of T cells related to inflammatory response, while LPS is known to increase the expression of FOXP3 gene, a marker of Treg cells related to inflammation regulation. The PBMC cell test group prepared under the above conditions was incubated for 5 days and then the cells were obtained and collected. In order to confirm the level of gene expression, first, the Easy-spin™ (DNA free) Total RNA Extraction Kit (Intron) was used to extract RNA and then the High Capacity RNA-to-cDNA Kit (ThermoFisher) was used to synthesize cDNA. A real-time PCR was conducted on the synthesized cDNA with the Rotor-Gene SYBR Green PCR kit (Qiagen) using a Rotor-Gene® Q (Qiagen) equipment according to the manufacturer's method and the mRNA expression of T-bet which is Th1 marker (effector cell marker) gene, GATA3 which is Th2 marker gene, RORγt which is Th17 marker gene, and FOXP3 which is Treg cell marker gene were measured. At this time, the expression level of B2M genes was measured as an internal control to correct the relative gene expression level between each test group. The base sequence of the primer used to confirm the expression of each gene is as follows.

```
B2M
                                        (SEQ ID NO. 4)
Forward: 5'-CCA GCA GAG AAT GGA AAG TC-3'

(SEQ ID NO. 5)
Reverse: 5'-GAT GCT TCT TAC ATG TCT CG-3'

T-bet
                                        (SEQ ID NO. 6)
Forward: 5'-CCC CAA GGA ATT GAC AGT TG-3'

(SEQ ID NO. 7)
Reverse) 5'-GGG AAA CTA AAG CTC ACA AAC-3'

GATA3
                                        (SEQ ID NO. 8)
Forward: 5'-CTG CAA TGC CTG TGG GCT C-3'

(SEQ ID NO. 9)
Reverse: 5'-GAC TGC AGG GAC TCT CGC T-3'

RORγt
                                        (SEQ ID NO. 10)
Forward: 5'-AAG ACT CAT CGC CAA AGC AT-3'

(SEQ ID NO. 11)
Reverse: 5'-TCC ACA TGC TGG CTA CAC A-3'

FOXP3
                                        (SEQ ID NO. 12)
Forward: 5'-TCA AGC ACT GCC AGG CG-3'

(SEQ ID NO. 13)
Reverse: 5'-CAG GAG CCC TTG TCG GAT-3'
```

As a result, as shown in FIGS. 2A-2D, it was confirmed that the *Lactobacillus paracasei* KBL382 and KBL385 strains, compared to *E. coli*, maintained the expression level of T-bet, GATA3, and RORγt genes, which are effector cell markers of inflammatory T cells, at a significantly low level, but significantly increased mRNA of FOXP3, a marker of Treg cells for maintaining immune homeostasis similarly to LPS.

Example 3. Verification of the Effect of *Lactobacillus paracasei* KBL382, KBL384 and KBL385 Strains on T-cell Immunoregulation (In Vitro Test)

Meanwhile, in order to verify T-cell immunoregulatory effect by *Lactobacillus paracasei* KBL382, KBL384 and KBL385 strains, the expression level of the inflammatory cytokines was verified when T-cells were activated in PBMC cells, and then followed by the treatment with said *paracasei* KBL382, KBL384 and KBL385 strains.

PBMC cells were seeded onto each well of a 96-well plate by 2×10$^5$ cells with an anti-CD3 antibody (1 μg/mL, ebioscience) to activate T cells, and then a *Lactobacillus paracasei* KBL382, KBL384 or KBL385 strain was added by 1×10$^7$ cells to be "bacteria:PBMC=50:1", based on the number of viable cells. As a control, *Escherichia coli* K12 (ATCC 10798) was added to each well by 1×10$^7$ cells based on the number of viable cells. After incubating the test group of T cells-activated PBMC cells prepared under the above conditions for 3 days, the supernatant was collected and the amount of each cytokine was measured using the BD cytometric Bead Array (CBA) human inflammation kit (Cat No. 551811) according to the manufacturer's method.

As a result, as shown in FIGS. 3A-3E, in the PBMC cell lines that T-cells were activated by addition of an anti-CD3 antibody, the *Lactobacillus paracasei* KBL382, KBL384 and KBL385 strains all significantly decreased the expression of IL-2, which is a cytokine of Th1, IL-4 and IL-13, which are respectively cytokines of IFNγ and Th2, and IL-17A, which is a cytokine of Th17, as compared to the test group treated only with the *E. coli*-added strain and PBS, while the anti-inflammatory cytokine IL-10 was remarkably increased in all of the three *Lactobacillus paracasei* strains used in the experiment, as compared to the test group treated only with PBS; it was confirmed that especially the KBL382 strain, among the three, significantly increased IL-10 as compared to the *E. coli* added group. The experiment results as above led to a conclusion that all of the *Lactobacillus paracasei* KBL382, KBL384 and KBL385 strains significantly decreased inflammatory cytokines of T-cells and increased anti-inflammatory cytokines.

Example 4. Verification of the Effect of *Lactobacillus paracasei* KBL382, KBL384 and KBL385 Strains on Enteritis Alleviation Effects (In Vivo Test)

The present example was to confirm whether the *Lactobacillus paracasei* KBL382, KBL384 and KBL385 strains showed the intestinal function improvement effects even in vivo. To this end, C57BL/6 mice were divided into groups of 10 mice each, and then fed tap water with 2% DSS dissolved therein for 9 days, and thereby inducing enteritis. At the same time, the mice in the control group were orally administered with 200 μL of PBS daily, and the mice in the test group were daily provided via an oral administration with 200 μL of each of the *Lactobacillus paracasei* KBL382, KBL384 or KBL385 strain which was diluted in PBS to be 2×10$^{10}$ CFU/mL so that the amount of daily administration could be set at 4×10$^9$ CFU. Then, during the 9 days in which enteritis was induced by DSS, the body weight changes of the mice in the control group and test group were measured daily, and on the 9$^{th}$ day after DSS was supplied, mice were subjected to autopsies to measure the length of the colon.

As a result, as shown in FIGS. 4A-4H, it was confirmed that regarding the body weight changes, the groups treated with KBL382, KBL384 and KBL385 strains all showed a significant effect on alleviating the weight loss, as compared to the mice in the control group with no treatment; regarding the colon length change, the width of decrease in the colon length was significantly improved in all the groups of three strains, as compared to the mice in the control group.

In addition, H&E staining was performed to measure the degree of inflammation in the test groups of KBL382 and KBL385 strains, and Myeloperoxidase (MPO) levels were measured in the tissues. After autopsy, in order to examine the lesions of the colon by H&E staining, the distal part of the colon was fixed in 10% neutral formalin solution, and then paraffin tissue specimens were sectioned with a thickness of 5 μm, stained with hematoxylin & eosin, and observed with an optical microscope. Further, for MPO measurement, colon tissue was, first, put in RIPA buffer to which a protease inhibitor was added, and was disrupted with a homogenizer. After centrifuging the disrupted tissue at 4° C. at 15,000×g for 10 minutes, MPO was measured using the supernatant according to the protocol of ELISA kit (Hycult Biotech, MPO, Mouse, cat. HK210-02).

As a result, as shown in FIGS. 4A-4H, it was confirmed through the H&E staining results, that the test groups that the two strains, KBL382 and KBL385, were administered all alleviated inflammation as compared to the control group, and the level of MPO was slightly decreased in the KBL385 test group and significantly decreased in the KBL382 test group. Using the colon tissues thus obtained were used to confirm the strengthening effect on tight junction of the intestinal tract wall.

Example 5. Effects of the *Lactobacillus paracasei* KBL382 and KBL385 Strains on Strengthening Intestinal Tract Wall Tight Junction In order to verify the effects of the *Lactobacillus paracasei* KBL382 and KBL385 strains on strengthening intestinal tract wall tight junction, the mRNA expression levels of genes involved in the intestinal tract wall tight junction were compared and measured in the cells isolated from the mouse colon tissue isolated in Example 4. To check the amount of gene expression, RNA was first extracted from tissues using the Easy-spin™ (DNA free) Total RNA Extraction Kit (Intron), and then cDNA was synthesized with the High Capacity RNA-to-cDNA Kit (ThermoFisher). The Rotor-gene SYBR green PCR kit (Qiagen) was used to measure in vivo the mRNA expression level of zonula occluden-1 (ZO-1), Claudin3 and MUC-4, which are the intestinal tract wall tight junction marker proteins, using a Rotor-Gene® Q (Qiagen). The expression level of the hypoxanthine-guanine phosphoribosyl-transferase (HPRT) gene was measured as a control to normalize the relative gene expression level between each test groups. The primer used to confirm the expression is prepared to be able to specifically bind to each gene as follows.

```
Zo-1
                                        (SEQ ID No. 14)
    Fw: 5'-ACC CGA AAC TGA TGC TGT GGA TAG-3'

(SEQ ID No. 15)
    Rw: 5'-AAA TGG CCG GGC AGA ACT TGT GTA-3'

Claudin3
                                        (SEQ ID No. 16)
    Fw: 5'-CAG ACG TCC GTC AGT TTT CG-3'

(SEQ ID No. 17)
    Rw: 5'-CAT GGC TGC TGG ACT TGA AC-3'

MUC-4
                                        (SEQ ID No. 18)
    Fw: 5'-GTC TCC CAT CAC GGT TCA GT-3'

(SEQ ID No. 19)
    Rw: 5'-TGT CAT TCC ACA CTC CCA GA-3'

HPRT
                                        (SEQ. ID No. 20)
    Fw: 5'-TTA TGG ACA GGA CTG AAA GAC-3'

(SEQ ID No. 21)
    Rw: 5'-GCT TTA ATG TAA TCC AGC AGG T-3'
```

Figures 5A, 5B, 5C:
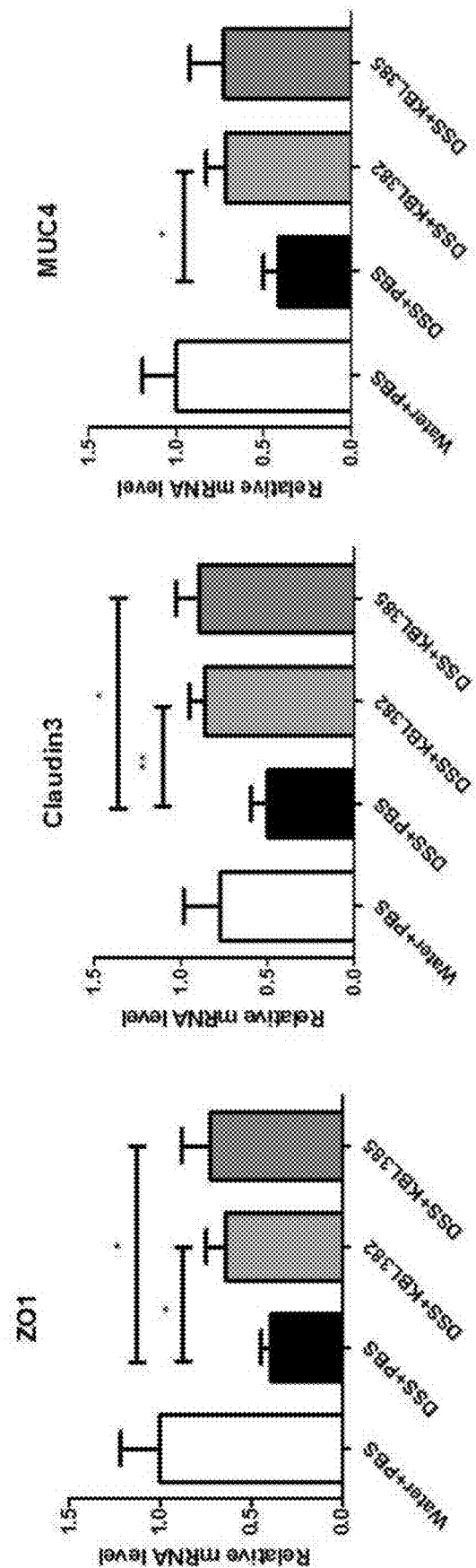
FIGS. 5A-5C illustrate the results of observing the effect of strengthening tight junctions of a KBL382 strain and a KBL385 strain of the present invention through the change in the expression level of the intestinal tract wall tight junction-related genes, (FIG. 5A) ZO1, (FIG. 5B) Claudin3, and (FIG. 5C) MUC4.

As a result, as shown in FIGS. 5A-5C, it was found that the levels of the three genes measured in the mice dosed with the KBL382 and KBL385 strains were increased as compared to the control group dosed with only PBS, and thereby the intestinal tract wall tight junction was recovered; accordingly, said strains can be used for treating the diseases such as IBD and IBS.

Example 6. Comparison of the Enteritis Alleviating Effects Between an Therapeutic Antibody for Enteritis and KBL382

Infliximab (product name Remicade) is a therapeutic recombinant antibody drug used as an injection for autoimmune diseases such as rheumatoid arthritis, ankylosing spondylitis, ulcerative colitis, Crohn's disease in adults, Crohn's disease in children, psoriasis, and psoriatic arthritis. The purpose of this study was to confirm the difference in effect on alleviating intestinal disease symptoms in vivo between the KBL382 strain and the infliximab.

For the comparison of the effects, after dividing C57BL/6 mice into groups of eight mice, the mice were fed tap water with 2% DSS dissolved therein for 9 days, inducing enteritis. At the same time, 200 μL of PBS was orally administered to the mice in the control group daily, while 200 μL of the KBL382 strain diluted in PBS to be 2×10$^{10}$ CFU/mL was orally administered to the mice in the test group daily so that the amount of daily administration could be set at 4×10$^9$ CFU. To the therapeutic antibody administration group, infliximab antibody was administered once on Day 3 to be a dose of 5 mg/kg per mouse.

Later, during the 9 days in which enteritis was induced by DSS, the body weight changes of the mice in the control group and test group were measured daily, and on the 9$^{th}$ day after DSS was supplied, mice were subjected to autopsies to measure the length of the colon.

Figure 6A:
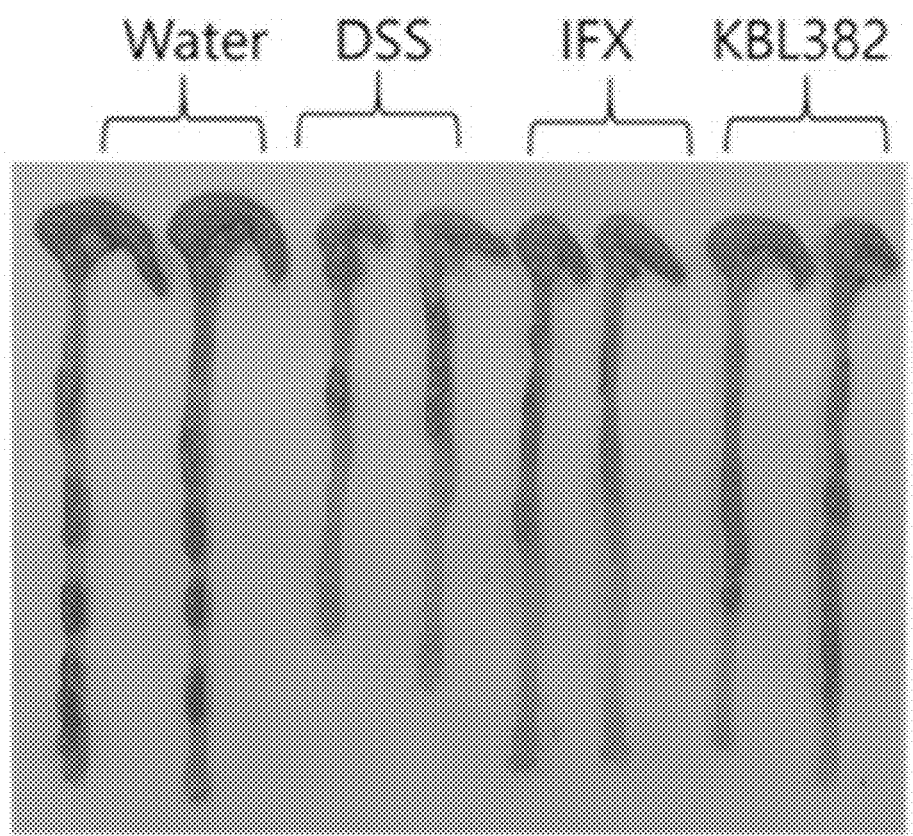
FIGS. 6A-6C illustrate the results of comparing the effects of (FIGS. 6A and 6B) recovering the length of colon and (FIG. 6C) improving body weight loss by a KBL382 strain of the present invention and infliximab, an antibody for treating enteritis, which is available in the market, in order to confirm the effect of alleviating enteritis by the KBL382 strain of the present invention.
Figure 6B:
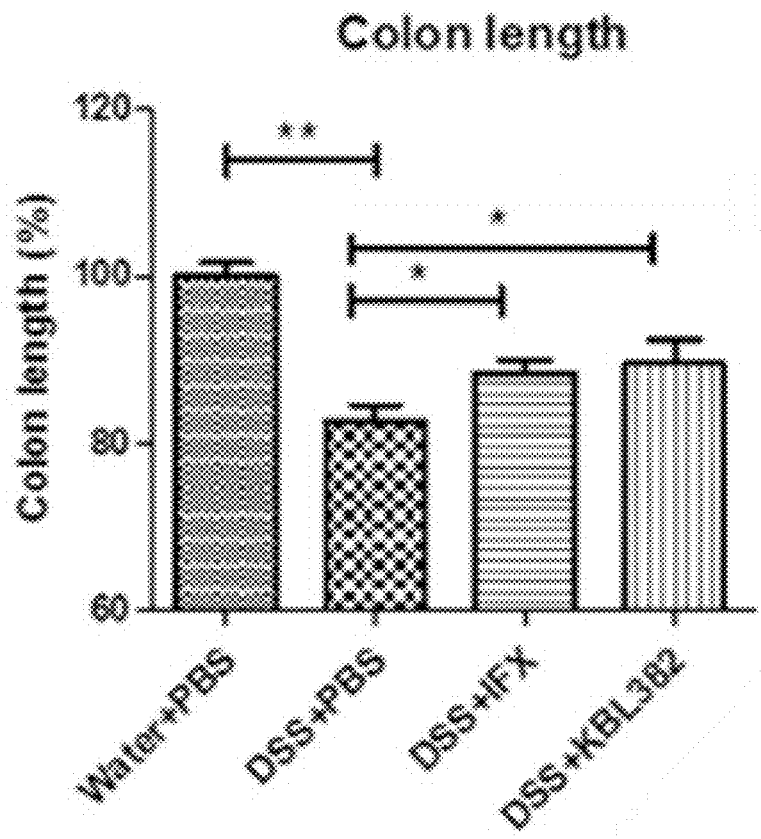

As a result, as shown in FIGS. 6A and 6B, regarding the colon length change, it was confirmed that the width of decrease in the colon length was significantly improved in the groups that KBL382 strain was treated and that infliximab was administered, compared to the mice in the control group. It was confirmed that the effect of improving the colon length of the group that KBL382 strain was treated was similar or rather higher than the group that infliximab was administered.

Figure 6C:
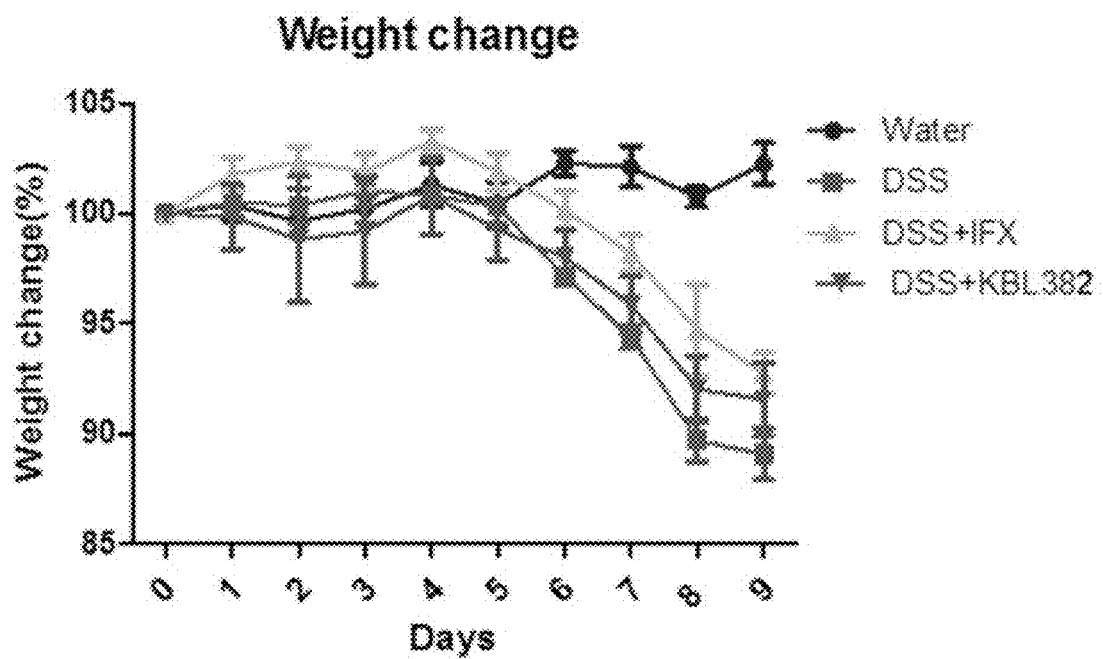

Regarding the change in body weights, as shown in FIG. 6C, the effect on body weight decrease was significantly improved in the groups that KBL382 strain was treated and that infliximab was administered, compared to the mice in the control group with no treatment. It was confirmed that the effect of alleviating the initial weight loss during five days after the administration was superior in the group that infliximab was administered over the group that KBL382 strain was treated, but later the improvement effect by infliximab was decreased, while the effect of the KBL382 strain-treated group on the weight loss was increased, showing similar effects between the two groups until the $9^{th}$ day. Accordingly, regarding the use of said strain for the treatment of inflammatory intestine diseases and irritable bowel syndrome, it was confirmed that a therapeutic effect similar to the commercially available therapeutic antibodies could be expected.

Example 7. Effects of KBL382 on Alleviation of Atopic Conditions

In order to verify the effect on atopic alleviation of the KBL382 strain, the NC/Nga mouse model, an animal model of atopic skin disease, was used.

After dividing NC/Nga mice into groups of nine mice, the back of each mouse was epilated from the lower ear to the upper tail and mice were left for 24 hours. Then, an ointment comprising *Dermatophagoides farinae* extract (DFE), a house dust mite (HDM) antigen, was applied once or twice a week for seven weeks onto the epilated portion so that each mouse could be treated with 100 mg of DFE, and thereby inducing atopic dermatitis. From the third week of dermatitis induction, 200 μL of PBS was orally administered to the mice in the control group daily; each of the KBL382 strain and *Lactobacillus rhamnosus* KBL365 strain, which was diluted in 200 μL of PBS to be at least $1\times10^9$ CFU/mouse, was orally administered to the mice in the test group by 200 μL daily. Then, during four weeks of administration of the bacteria, dermatitis scores of the mice in the control and test group were measured weekly, and on the $4^{th}$ week after the administration of the bacteria, the mouse's scratching time and skin thickness, and IgE concentration-in-blood after conducting autopsies of mice were measured.

7-1. Evaluation of Dermatitis Score

To evaluate DFE-induced skin lesions, the dermatitis score was measured through the following method. Skin conditions were monitored by taking pictures for 4 weeks at one week intervals from the 3rd week since the strain had been administered. Four indicators of dryness, edema, erythema/hemorrhage, and erosion/excoriation of the skin were checked. The total score was evaluated with 0 points for no lesion, 1 point for mild, 2 points for moderate, and 3 points for severe.

Figure 7A:
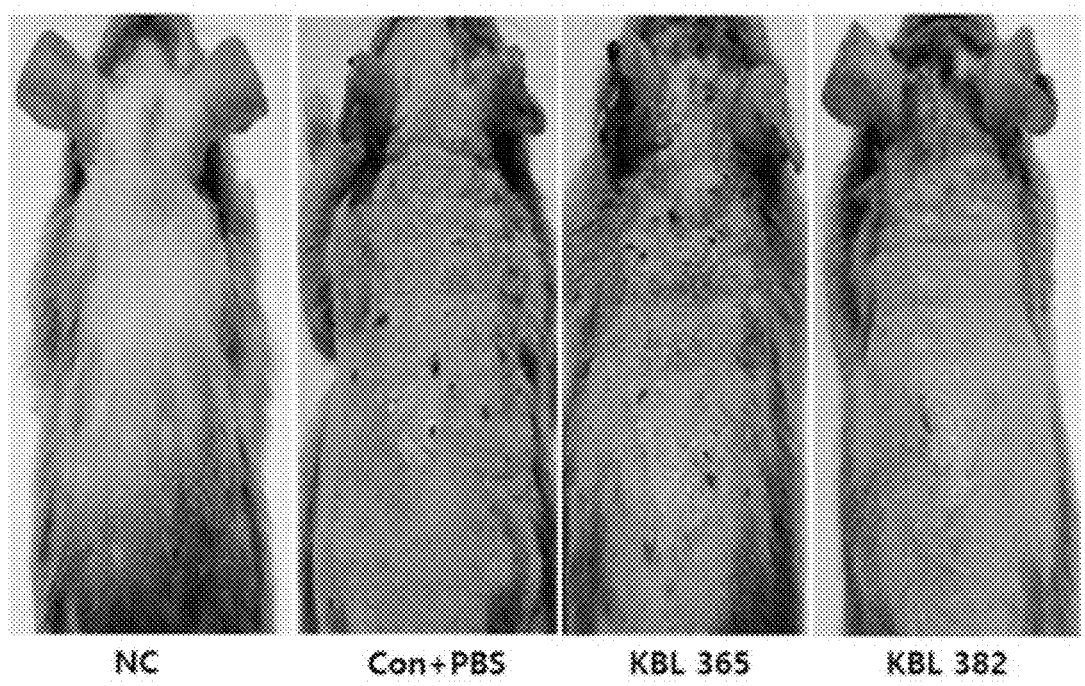
FIGS. 7A-7F illustrate the results of observing (FIGS. 7A and 7B) the dermatitis score measurement, (FIG. 7C) the itching-alleviating effect, (FIGS. 7D and 7E) the skin thickness lowering effect and (FIG. 7F) the IgE concentration-in-blood lowering effect by the administration of a KBL382 strain of the present invention to animal models that atopic dermatitis was induced, in order to confirm the effect of alleviating atopic symptoms by the KBL382 strain.
Figure 7B:
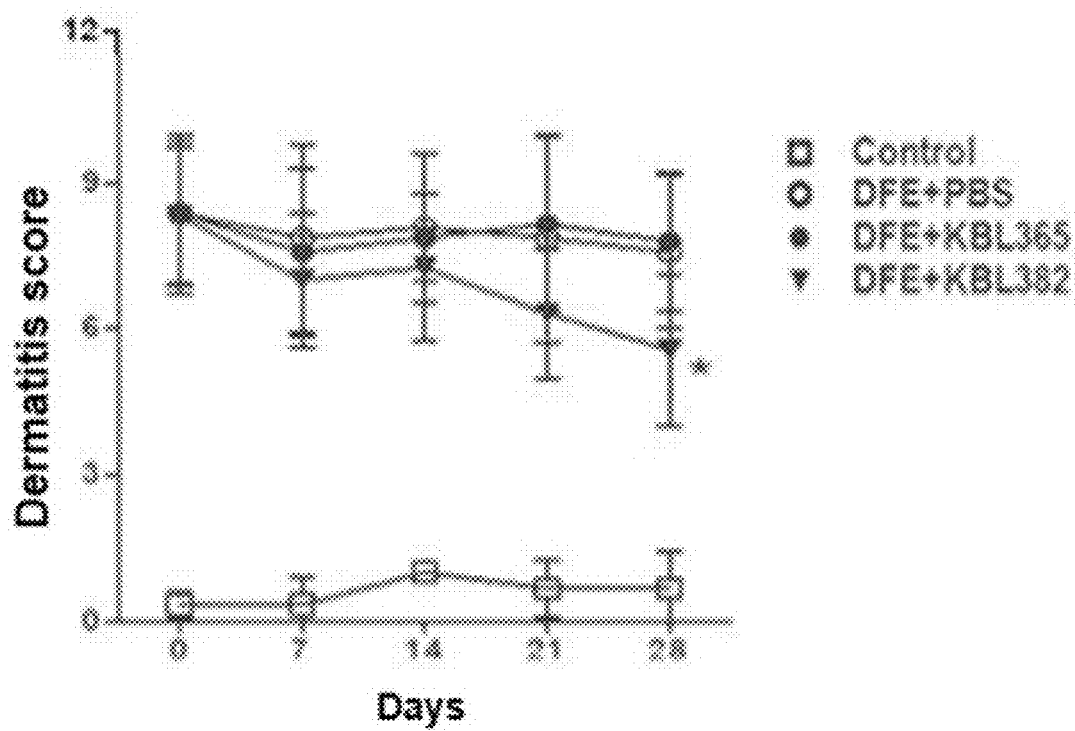

As a result, as shown in FIGS. 7A and 7B, the dermatitis score was significantly reduced in the group dosed with KBL382 strain, compared to the control group (negative) where atopic dermatitis was induced, and the group that the KBL365 strain was administered. As a result, the effect of alleviating atopic dermatitis score according to the intake of KBL382 strain was verified.

7-2 Effects on Alleviating Itching Symptoms

In order to verify the effect of alleviating itching according to the administration of KBL382 strain in the mouse models suffering from atopic dermatitis induced by DFE, the number of scratches was measured for the mouse during 10 minutes after 4 weeks of strain administration.

Figure 7C:
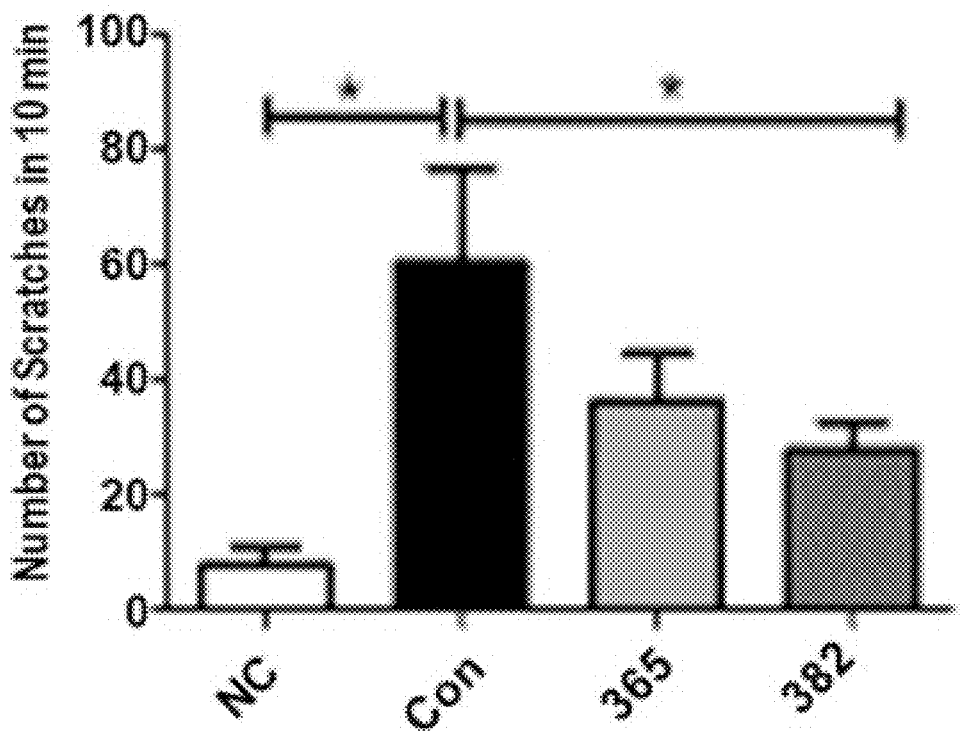

As a result, as can be seen in FIG. 7C, it appeared that the number of scratches was significantly reduced in the test group that KBL382 was administered, as compared to the PBS administration group, which confirmed that the itching symptoms of atopic dermatitis were alleviated by the administration of the KBL382 strain.

7-3. Decrease of Skin Thickness

Figure 7D:
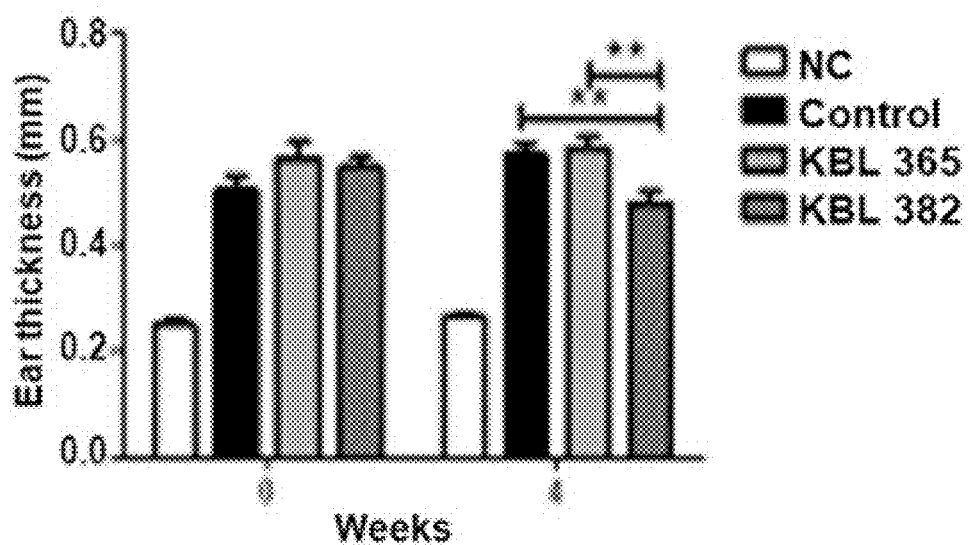
Figure 7E:
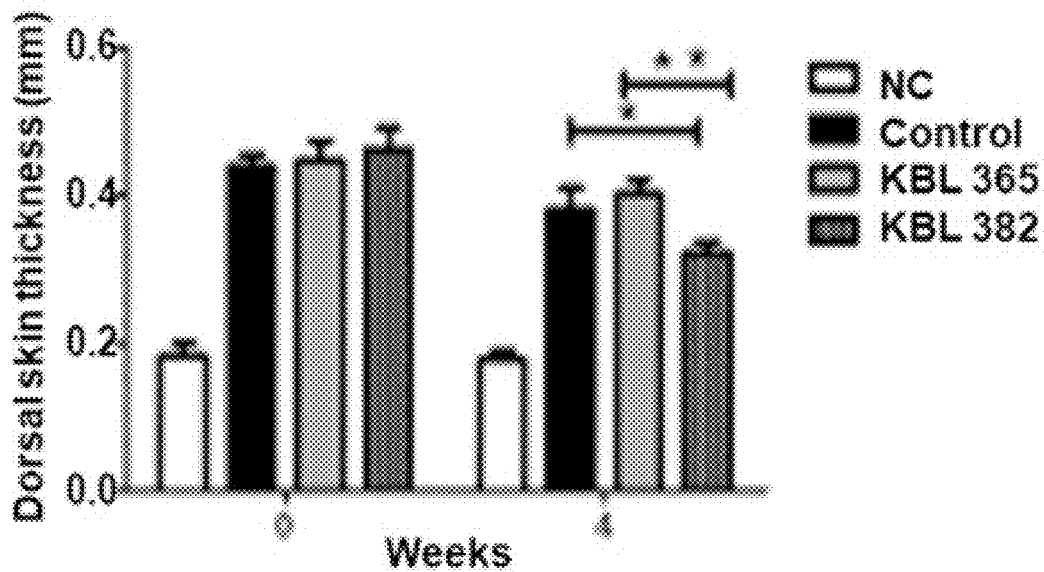

In order to verify the effect of decreasing the skin thickness after administration of KBL382 to mouse models suffering from atopic dermatitis induced by DFE, the mouse ear thickness and dorsal skin thickness were measured with calipers four weeks after the strain was administered, and the relief of edema symptom due to atopic dermatitis was observed. As a result, as can be seen in FIGS. 7D and 7E, it was observed that in the test group dosed with KBL382, the ear and skin thicknesses were significantly reduced, as compared to the control group and the KBL365-administered group.

7-4. Decrease in IgE Concentration-in-Blood

Figure 7F:
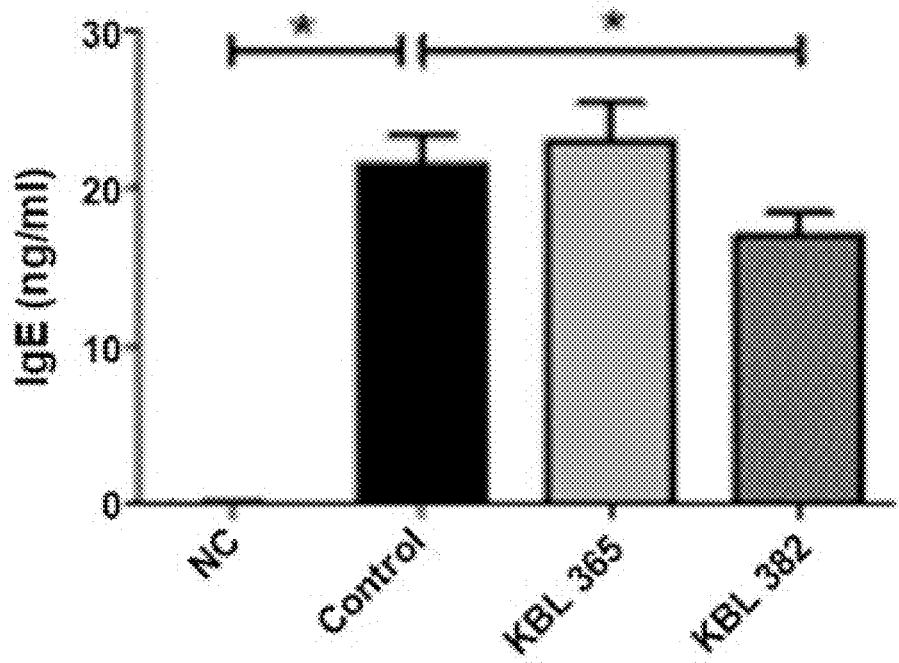

It has been found that the concentration of IgE in patients having atopic dermatitis has mostly increased as clinical severity of atopic dermatitis increased (Matsumoto M, J. Immunol. 1999). Thus, the concentration of IgE, a representative hematologic factor appearing as atopic dermatitis arises, was measured by collecting blood three weeks after the strain was administered, separating serum therefrom and using Mouse IgE ELISA Set (Cat No. 555248, BD OptEIA™). As a result, as shown in FIG. 7F, it was found that the concentration of IgE-in-blood was significantly decreased in the test group that KBL382 was orally administered, which indicated the effect of treating atopic dermatitis after intake of KBL382.

Specific aspects of the present invention have been described in detail above, and it is obvious to those skilled in the art that these specific aspects are only preferred embodiments, and the scope of the present invention is not limited thereby. Therefore, the scope of the present invention is substantially defined by the following claims, with equivalents to the claims.

Name of Depository Organization: Korean Collection for Type Cultures, Korea Research Institute of Bioscience and Biotechnology (KRIBB), 181, Ipsin-gil, Jeongeup-si, Jeollabuk-do, 56212, Republic of Korea Accession No.: KCTC13509BP Accession Date: 20180417

Name of Depository Organization: Korean Collection for Type Cultures, Korea Research Institute of Bioscience and Biotechnology (KRIBB), 181, Ipsin-gil, Jeongeup-si, Jeollabuk-do, 56212, Republic of Korea Accession No.: KCTC13510BP Accession Date: 20180417

Name of Depository Organization: Korean Collection for Type Cultures, Korea Research Institute of Bioscience and Biotechnology (KRIBB), 181, Ipsin-gil, Jeongeup-si, Jeollabuk-do, 56212, Republic of Korea
Accession No.: KCTC13511BP
Accession Date: 20180417

INDUSTRIAL APPLICABILITY

The strains of *Lactobacillus paracasei* KBL382 (Accession No. KCTC13509BP), *Lactobacillus paracasei* KBL384 (Accession No. KCTC13510BP), and *Lactobacillus paracasei* KBL385 (Accession No. KCTC13511BP) according to the present invention have excellent anti-inflammatory and immunomodulatory functions, has a superb strengthening effect on tight junction of the intestinal tract wall, suppresses enteritis-induced weight loss and colon length reduction, thereby exhibiting a therapeutic effect for enteritis, and weakens allergic reaction of cells, and significantly alleviates the symptoms of atopic dermatitis, and thereby providing improvement of allergic diseases. Therefore, a single strain can achieve enhancing anti-inflammatory effects, strengthening immunity, improving intestinal health functions, and alleviating allergic diseases, and thus can be useful as a probiotic material.

Sequence List Free Text

An electronic file of Sequence List is attached.

The invention claimed is:

1. A composition in a dry dosage form of capsule, tablet, or powder, comprising: at least one lyophilized strain of *Lactobacillus paracasei* selected from *Lactobacillus paracasei* KBL384 with Accession No. KCTC13510BP, *Lactobacillus paracasei* KBL385 with Accession No. KCTC13511BP, or lyophilized cultures of said strain.

2. The composition according to claim 1, wherein strain KBL384 comprises 16s rDNA sequence of SEQ ID NO: 2.

3. The composition according to claim 1, wherein strain KBL385 comprises 16s rDNA sequence of SEQ ID NO: 3.

4. The composition according to claim 1, wherein the composition is a food composition.

5. The composition according to claim 4, wherein said food composition is a health functional food composition for improvement of intestinal health.

6. The composition according to claim 4, wherein said food composition is a health functional food composition for improving allergic symptoms.

7. The composition according to claim 4 wherein said food composition is a health functional food composition for alleviating autoimmune disease or inflammatory disease.

8. The composition according to claim 1, wherein the composition is a food additive composition.

9. The composition according to claim 1, wherein the composition is a pharmaceutical composition for the treatment or prevention of intestinal disease.

10. The composition according to claim 9, wherein said intestinal disease is selected from abdominal bloating, abdominal discomfort, infectious diarrhea caused by pathogenic microorganisms, gastroenteritis, inflammatory bowel diseases, neurogenical intestinitis syndrome, irritable bowel syndrome, overgrowth of small intestinal microorganisms and intestinal feeding diarrhea.

11. The composition according to claim 1, wherein the composition is a pharmaceutical composition for the treatment or prevention of allergic disease.

12. The composition according to claim 11, wherein said allergic disease is atopic dermatitis, urticaria, allergic rhinitis, allergic conjunctivitis, asthma, food allergy or anaphylactic shock.

13. The composition according to claim 1, wherein the composition is a pharmaceutical composition for the treatment or prevention of autoimmune disease.

14. The composition according to claim 1, wherein the composition is a pharmaceutical composition for the treatment or prevention of inflammatory disease.

15. A method for treating, alleviating or preventing intestinal disease, allergic disease, autoimmune disease or inflammatory disease comprising administering a therapeutically effective amount the composition according to claim 1.

16. A composition in a dry dosage form of capsule, tablet, or powder, comprising:
   at least one lyophilized strain of *Lactobacillus paracasei* KBL384 with Accession No. KCTC13510BP, *Lactobacillus paracasei* KBL385 with Accession No. KCTC13511BP, or lyophilized cultures of said strain, and
   a pharmaceutically acceptable excipient, diluent, or carrier.

17. The composition according to claim 16, wherein the composition is in solid form.

* * * * *

SEQUENCE LISTING

<160> NUMBER OF SEQ ID NOS: 21

<210> SEQ ID NO 1
<211> LENGTH: 1472
<212> TYPE: DNA
<213> ORGANISM: Lactobacillus paracasei

<400> SEQUENCE: 1

```
gcaggtggcg ggtgctatac atgcagtcga cgagttctcg ttgatgatcg gtgcttgcac      60
cgagattcaa catggaacga gtggcggacg ggtgagtaac acgtgggtaa cctgccctta     120
agtgggggat aacatttgga aacagatgct aataccgcat agatccaaga accgcatggt     180
tcttggctga aagatggcgt aagctatcgc ttttggatgg acccgcggcg tattagctag     240
ttggtgaggt aatggctcac caaggcgatg atacgtagcc gaactgagag gttgatcggc     300
cacattggga ctgagacacg gcccaaactc ctacgggagg cagcagtagg gaatcttcca     360
caatggacgc aagtctgatg gagcaacgcc gcgtgagtga agaaggcttt cgggtcgtaa     420
aactctgttg ttggagaaga atggtcggca gagtaactgt tgtcggcgtg acggtatcca     480
accagaaagc cacggctaac tacgtgccag cagccgcggt aatacgtagg tggcaagcgt     540
tatccggatt tattgggcgt aaagcgagcg caggcggttt tttaagtctg atgtgaaagc     600
cctcggctta accgaggaag cgcatcggaa actgggaaac ttgagtgcag aagaggacag     660
tggaactcca tgtgtagcgg tgaaatgcgt agatatatgg aagaacacca gtggcgaagg     720
cggctgtctg gtctgtaact gacgctgagg ctcgaaagca tgggtagcga acaggattag     780
ataccctggt agtccatgcc gtaaacgatg aatgctaggt gttggagggt ttccgccctt     840
cagtgccgca gctaacgcat taagcattcc gcctggggag tacgaccgca aggttgaaac     900
tcaaaggaat tgacggggc ccgcacaagc ggtggagcat gtggtttaat tcgaagcaac     960
gcgaagaacc ttaccaggtc ttgacatctt ttgatcacct gagagatcag gtttcccctt    1020 cggggggcaaa atgacaggtg gtgcatggtt gtcgtcagct cgtgtcgtga gatgttgggt    1080
taagtcccgc aacgagcgca acccttatga ctagttgcca gcatttagtt gggcactcta    1140
gtaagactgc cggtgacaaa ccggaggaag gtggggatga cgtcaaatca tcatgcccct    1200
tatgacctgg gctacacacg tgctacaatg gatggtacaa cgagttgcga ccgcgagg     1260 tcaagctaat ctcttaaagc cattctcagt tcggactgta ggctgcaact cgcctacacg    1320
aagtcggaat cgctagtaat cgcggatcag cacgccgcgg tgaatacgtt cccgggcctt    1380
gtacacaccg cccgtcacac catgagagtt tgtaacaccc gaagccggtg gcgtaaccct    1440
ttagggagcg agcgtctaag tggctcacgc ct                                   1472
```

<210> SEQ ID NO 2
<211> LENGTH: 1479
<212> TYPE: DNA
<213> ORGANISM: Lactobacillus paracasei

<400> SEQUENCE: 2

| | | | | | |
|---|---|---|---|---|---|
| gccagtgggg | ggggtgctat | acatgcagtc | gaacgagttc | tcgttgatga | tcggtgcttg | 60 |
| caccgagatt | caacatggaa | cgagtggcgg | acgggtgagt | aacacgtggg | taacctgccc | 120 |
| ttaagtgggg | gataacattt | ggaaacagat | gctaataccg | catagatcca | agaaccgcat | 180 |
| ggttcttggc | tgaaagatgg | cgtaagctat | cgcttttgga | tggacccgcg | gcgtattagc | 240 |
| tagttggtga | ggtaatggct | caccaaggcg | atgatacgta | gccgaactga | gaggttgatc | 300 |
| ggccacattg | ggactgagac | acggcccaaa | ctcctacggg | aggcagcagt | agggaatctt | 360 |
| ccacaatgga | cgcaagtctg | atggagcaac | gccgcgtgag | tgaagaaggc | tttcgggtcg | 420 |
| taaaactctg | ttgttggaga | agaatggtcg | gcagagtaac | tgttgtcggc | gtgacggtat | 480 |
| ccaaccagaa | agccacggct | aactacgtgc | cagcagccgc | ggtaatacgt | aggtggcaag | 540 |
| cgttatccgg | atttattggg | cgtaaagcga | gcgcaggcgg | ttttttaagt | ctgatgtgaa | 600 |
| agccctcggc | ttaaccgagg | aagcgcatcg | gaaactggga | aacttgagtg | cagaagagga | 660 |
| cagtggaact | ccatgtgtag | cggtgaaatg | cgtagatata | tggaagaaca | ccagtggcga | 720 |
| aggcggctgt | ctggtctgta | actgacgctg | aggctcgaaa | gcatgggtag | cgaacaggat | 780 |
| tagataccct | ggtagtccat | gccgtaaacg | atgaatgcta | ggtgttggag | ggtttccgcc | 840 |
| cttcagtgcc | gcagctaacg | cattaagcat | tccgcctggg | gagtacgacc | gcaaggttga | 900 |
| aactcaaagg | aattgacggg | ggcccgcaca | agcggtggag | catgtggttt | aattcgaagc | 960 |
| aacgcgaaga | accttaccag | gtcttgacat | cttttgatca | cctgagagat | caggtttccc | 1020 |
| cttcggggc | aaaatgacag | gtggtgcatg | gttgtcgtca | gctcgtgtcg | tgagatgttg | 1080 |
| ggttaagtcc | cgcaacgagc | gcaacccctta | tgactagttg | ccagcattta | gttgggcact | 1140 |
| ctagtaagac | tgccggtgac | aaaccggagg | aaggtgggga | tgacgtcaaa | tcatcatgcc | 1200 |
| ccttatgacc | tgggctacac | acgtgctaca | atggatggta | caacgagttg | cgagaccgcg | 1260 |
| aggtcaagct | aatctcttaa | agccattctc | agttcggact | gtaggctgca | actcgcctac | 1320 |
| acgaagtcgg | aatcgctagt | aatcgcggat | cagcacgccg | cggtgaatac | gttcccgggc | 1380 |
| cttgtacaca | ccgcccgtca | caccatgaga | gtttgtaaca | cccgaagccg | gtggcgtaac | 1440 |
| cctttaggga | gcgagccgtc | taaggtgaac | caaagtttg | | | 1479 |

<210> SEQ ID NO 3
<211> LENGTH: 1473
<212> TYPE: DNA
<213> ORGANISM: Lactobacillus paracasei

<400> SEQUENCE: 3

| | | | | | |
|---|---|---|---|---|---|
| gcagttgggg | gggagctata | catgcagtcg | acgagttctc | gttgatgatc | ggtgcttgca | 60 |
| ccgagattca | acatggaacg | agtggcggac | gggtgagtaa | cacgtgggta | acctgccctt | 120 |
| aagtggggga | taacatttgg | aaacagatgc | taataccgca | tagatccaag | aaccgcatgg | 180 |
| ttcttggctg | aaagatggcg | taagctatcg | cttttggatg | acccgcggc | gtattagcta | 240 |
| gttggtgagg | taatggctca | ccaaggcgat | gatacgtagc | cgaactgaga | ggttgatcgg | 300 |
| ccacattggg | actgagacac | ggcccaaact | cctacgggag | gcagcagtag | ggaatcttcc | 360 |
| acaatggacg | caagtctgat | ggagcaacgc | cgcgtgagtg | aagaaggctt | tcgggtcgta | 420 |

```
aaactctgtt gttggagaag aatggtcggc agagtaactg ttgccggcgt gacggtatcc    480
aaccagaaag ccacggctaa ctacgtgcca gcagccgcgg taatacgtag gtggcaagcg    540
ttatccggat ttattgggcg taaagcgagc gcaggcggtt ttttaagtct gatgtgaaag    600
ccctcggctt aaccgaggaa gcgcatcgga aactgggaaa cttgagtgca gaagaggaca    660
gtggaactcc atgtgtagcg gtgaaatgcg tagatatatg gaagaacacc agtggcgaag    720
gcggctgtct ggtctgtaac tgacgctgag gctcgaaagc atgggtagcg aacaggatta    780
gataccctgg tagtccatgc cgtaaacgat gaatgctagg tgttggaggg tttccgccct    840
tcagtgccgc agctaacgca ttaagcattc cgcctgggga gtacgaccgc aaggttgaaa    900
ctcaaaggaa ttgacggggg cccgcacaag cggtggagca tgtggtttaa ttcgaagcaa    960
cgcgaagaac cttaccaggt cttgacatct tttgatcacc tgagagatca ggtttcccct   1020 tcggggggcaa aatgacaggt ggtgcatggt tgtcgtcagc tcgtgtcgtg agatgttggg   1080
ttaagtcccg caacgagcgc aaccctatg actagttgcc agcatttagt tgggcactct   1140
agtaagactg ccggtgacaa accggaggaa ggtggggatg acgtcaaatc atcatgcccc   1200
ttatgacctg ggctacacac gtgctacaat ggatggtaca acgagttgcg agaccgcgag   1260
gtcaagctaa tctcttaaag ccattctcag ttcggactgt aggctgcaac tcgcctacac   1320
gaagtcggaa tcgctagtaa tcgcggatca gcacgccgcg gtgaatacgt tcccgggcct   1380
tgtacacacc gcccgtcaca ccatgagagt ttgtaacacc cgaagccggt ggcgtaaccc   1440
tttagggagc gagccgtcta agtgtacaaa gtt                                 1473
```

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ccagcagaga atggaaagtc                                                  20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gatgcttctt acatgtctcg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ccccaaggaa ttgacagttg                                                  20

<210> SEQ ID NO 7
<211> LENGTH: 21
<212> TYPE: DNA
<213> ORGANISM: Artificial Sequence
<220> FEATURE:

<223> OTHER INFORMATION: primer

<400> SEQUENCE: 7
gggaaactaa agctcacaaa c                                              21

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ctgcaatgcc tgtgggctc                                                 19

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gactgcaggg actctcgct                                                 19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aagactcatc gccaaagcat                                                20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
tccacatgct ggctacaca                                                 19

<210> SEQ ID NO 12
<211> LENGTH: 17
<212> TYPE: DNA
<213> ORGANISM: Artificial Sequence
<220> FEATURE:
<223> OTHER INFORMATION: primer

<400> SEQUENCE: 12
tcaagcactg ccaggcg                                                   17

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
caggagccct tgtcggat                                                  18

-continued

```
<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
acccgaaact gatgctgtgg atag                                              24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
aaatggccgg gcagaacttg tgta                                              24

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cagacgtccg tcagttttcg                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
catggctgct ggacttgaac                                                   20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtctcccatc acggttcagt                                                   20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tgtcattcca cactcccaga                                                   20

<210> SEQ ID NO 20
<211> LENGTH: 21
<212> TYPE: DNA
<213> ORGANISM: Artificial Sequence
<220> FEATURE:
<223> OTHER INFORMATION: primer
```

```
<400> SEQUENCE: 20
ttatggacag gactgaaaga c                                              21

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
gctttaatgt aatccagcag gt                                             22
```